(12) United States Patent
Bennett et al.

(10) Patent No.: US 10,178,989 B2
(45) Date of Patent: *Jan. 15, 2019

(54) SURGICAL SUTURE SYSTEM, TISSUE RESTRAINTS, AND TISSUE ANCHORS

(71) Applicant: ZIPTEK LLC, Sarasota, FL (US)

(72) Inventors: William F Bennett, Sarasota, FL (US); Ramses Galaz Mendez, Hermosillo (MX); Daniel Francisco Gomez Romo, Hermosillo (MX)

(73) Assignee: Ziptek LLC., Sarasota, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/076,088

(22) Filed: Mar. 21, 2016

(65) Prior Publication Data

US 2017/0325802 A1   Nov. 16, 2017

Related U.S. Application Data

(63) Continuation of application No. 13/664,717, filed on Oct. 31, 2012, now Pat. No. 9,307,979, which is a (Continued)

(51) Int. Cl.
*A61B 17/04* (2006.01)
*A61B 17/06* (2006.01)
(Continued)

(52) U.S. Cl.
CPC ...... *A61B 17/0401* (2013.01); *A61B 17/0466* (2013.01); *A61B 17/06166* (2013.01);
(Continued)

(58) Field of Classification Search
CPC ............ A61B 17/0401; A61B 17/0466; A61B 17/06166; A61B 2017/0404; A61B 2017/0427; A61B 2017/0438; A61B 2017/044; A61B 2017/0441; A61B 2017/045; A61B 2017/0456; A61B 2017/0462; A61B 2017/06176
See application file for complete search history.

(56) References Cited

U.S. PATENT DOCUMENTS

| | | | | |
|---|---|---|---|---|
| 5,725,556 A * | 3/1998 | Moser | ................ | A61B 17/0487 128/898 |
| 9,259,217 B2 * | 2/2016 | Fritzinger | .......... | A61B 17/0401 |
| 9,307,979 B1 * | 4/2016 | Bennett | ............ | A61B 17/06166 |

* cited by examiner

*Primary Examiner* — Julian W Woo
(74) *Attorney, Agent, or Firm* — Frijouf, Rust & Pyle, P.A.

(57) ABSTRACT

A surgical suture system, tissue restraint/suture capture and tissue anchor for tissue repair and reattachment of torn tissue to a tissue substrate, medical, veterinary or dental prosthesis or medical implant. The system includes a plurality of tissue restraints/suture captures which each include a central locking aperture sized and configured to receive a beaded suture member passed therethrough which minimizes longitudinal tensioning and/or restraining movement, the "GO" force, of a beaded suture member in the forwardly direction through the locking apertures for suture tightening and which maximizes "NO-GO" force to pull the suture in the reverse direction. Uniquely configured tissue anchors and other medically implantable devices securely receive one of the tissue restraints/suture captures for tensioning of a suture member between tissue and the tissue anchor.

10 Claims, 36 Drawing Sheets

Related U.S. Application Data continuation-in-part of application No. 13/281,963, filed on Oct. 26, 2011, now Pat. No. 8,845,686, and a continuation-in-part of application No. 12/912,313, filed on Oct. 26, 2010, now Pat. No. 8,814,904.

(60) Provisional application No. 61/709,481, filed on Oct. 4, 2012.

(51) Int. Cl.
*A61B 17/84* (2006.01)
*A61F 2/36* (2006.01)

(52) U.S. Cl.
CPC .......... *A61B 17/842* (2013.01); *A61F 2/3662* (2013.01); *A61B 2017/044* (2013.01); *A61B 2017/0404* (2013.01); *A61B 2017/045* (2013.01); *A61B 2017/0414* (2013.01); *A61B 2017/0417* (2013.01); *A61B 2017/0427* (2013.01); *A61B 2017/0438* (2013.01); *A61B 2017/0441* (2013.01); *A61B 2017/0456* (2013.01); *A61B 2017/0462* (2013.01); *A61B 2017/06176* (2013.01); *A61F 2002/368* (2013.01)

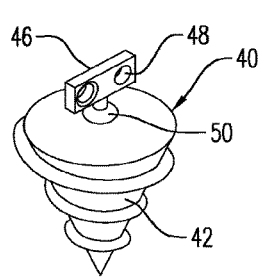
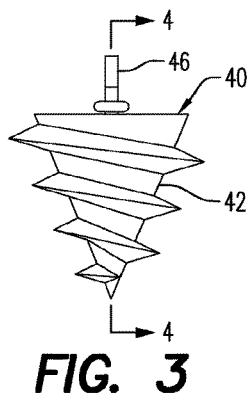
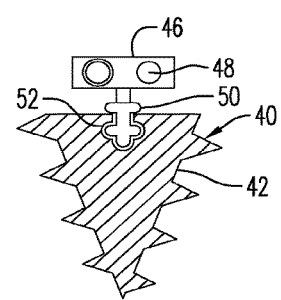
FIG. 2　　　FIG. 3　　　FIG. 4
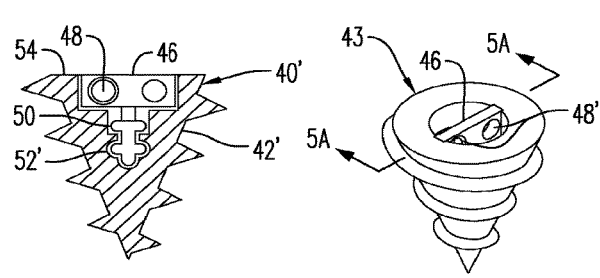
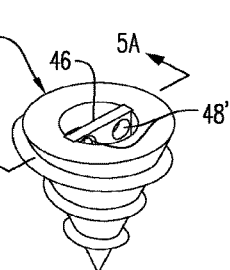
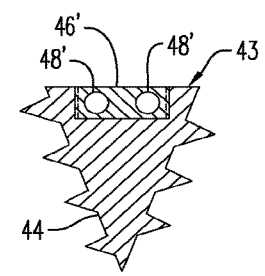
FIG. 4A　　　FIG. 5　　　FIG. 5A

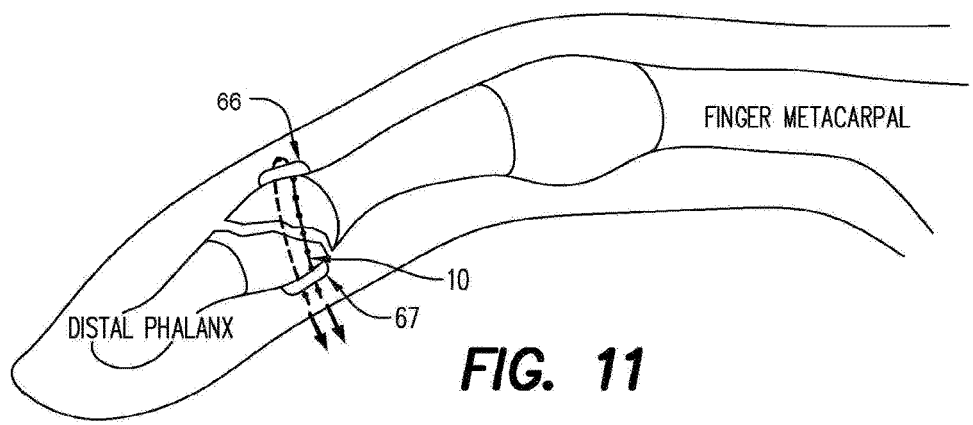
FIG. 11
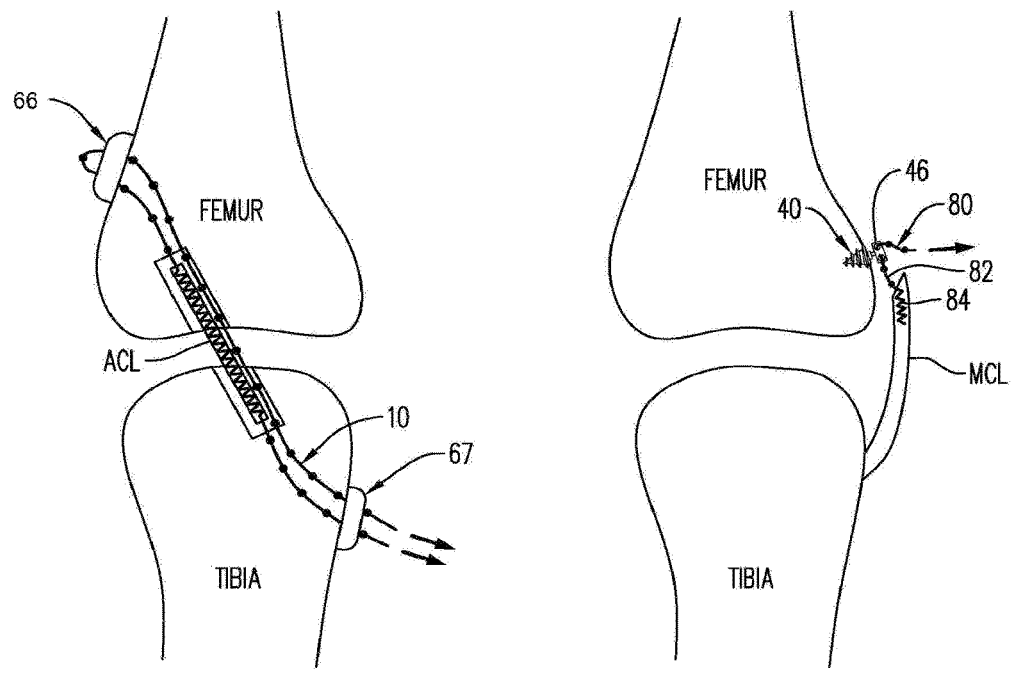
FIG. 12
FIG. 13

HIP LABRAL REPAIR

DISTAL BICEPS REPAIR

ANKLE SYNDESMOTIC
DISRUPTION

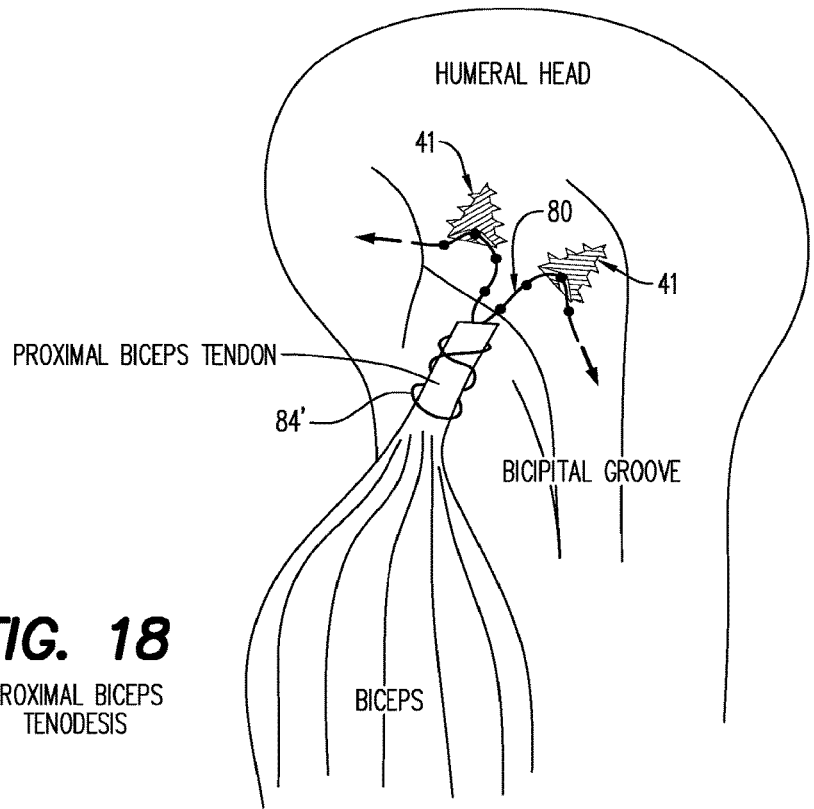
FIG. 18
PROXIMAL BICEPS TENODESIS
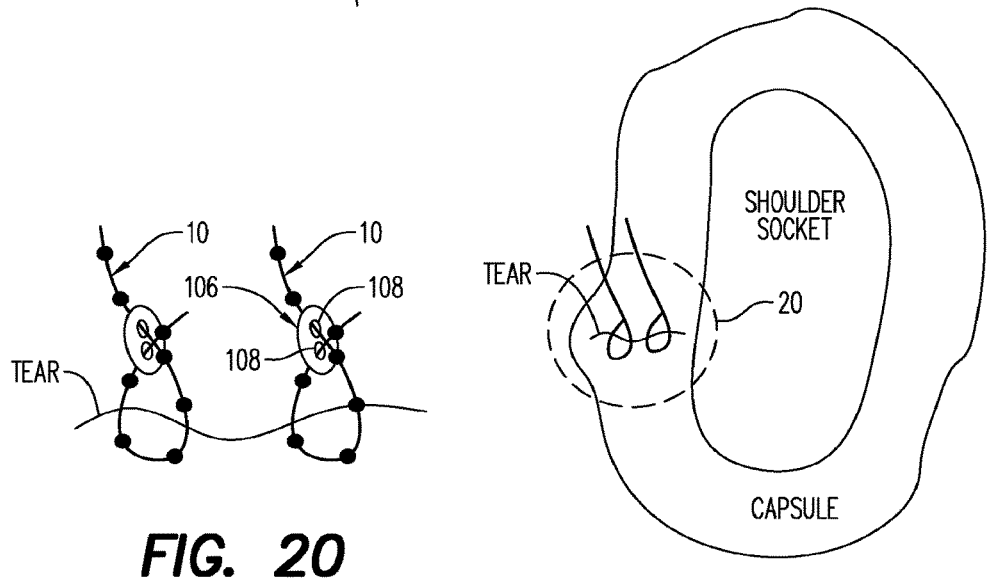
FIG. 20
FIG. 19
JOINT CAPSULE REPAIR WITH FREE CAPTURE WITHOUT ANCHOR

SHOULDER LABRAL REPAIR

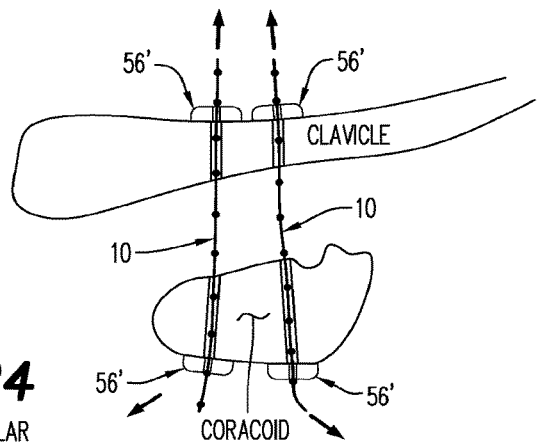
FIG. 24
CORACOCLAVICULAR
LIGAMENT REPAIR
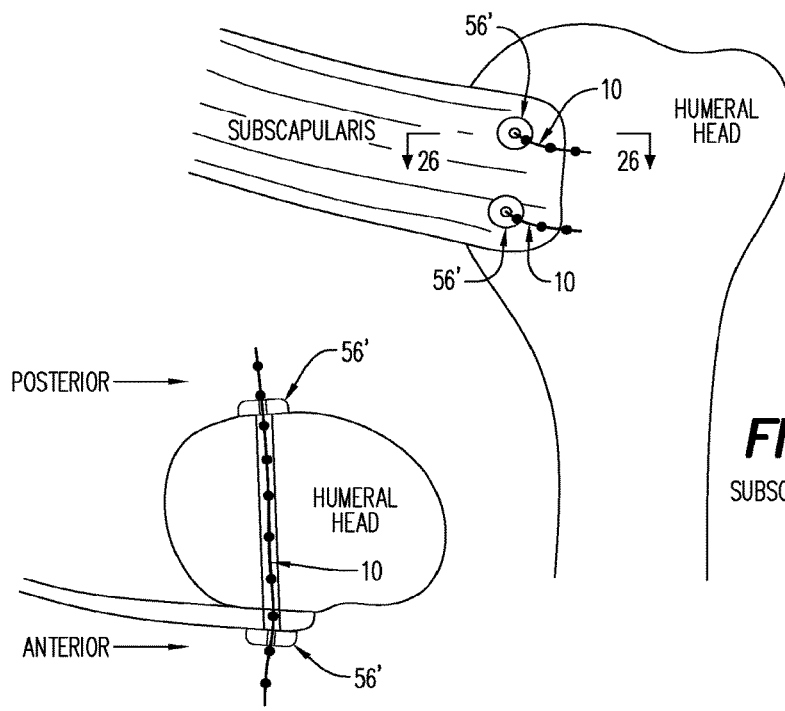
FIG. 25
SUBSCAPULARIS REPAIR
FIG. 26

ROTATOR CUFF
SINGLE ROW REPAIR

DOUBLE ROW
REPAIR

MENISCAL REPAIR
SAGITTAL VIEW

MENISCAL REPAIR
FIXED OR WITH
INTERFACE

MENISCAL REPAIR
MULTIPLE REPAIRS

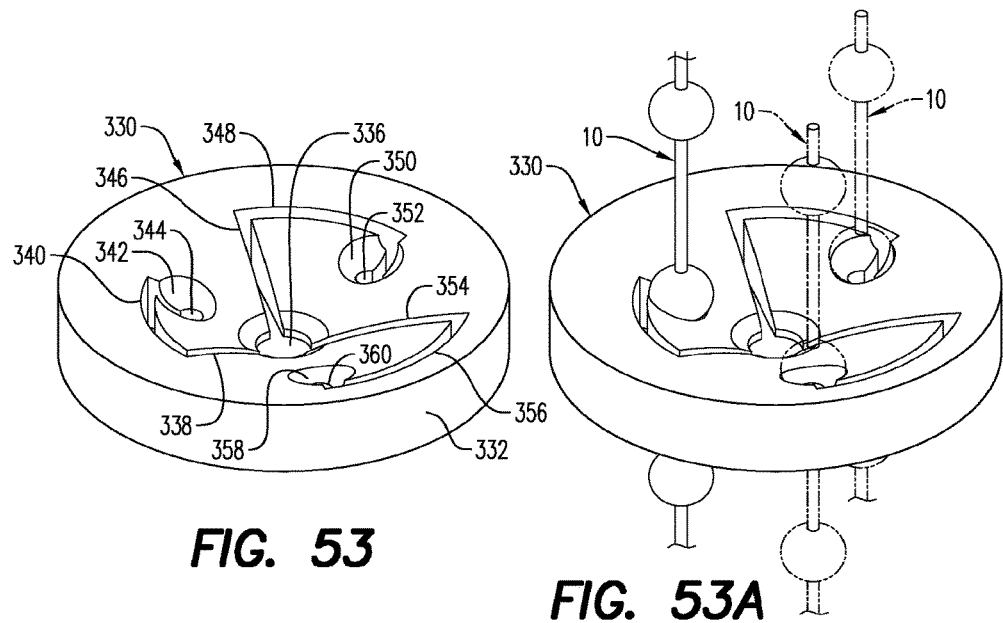
FIG. 53
FIG. 53A
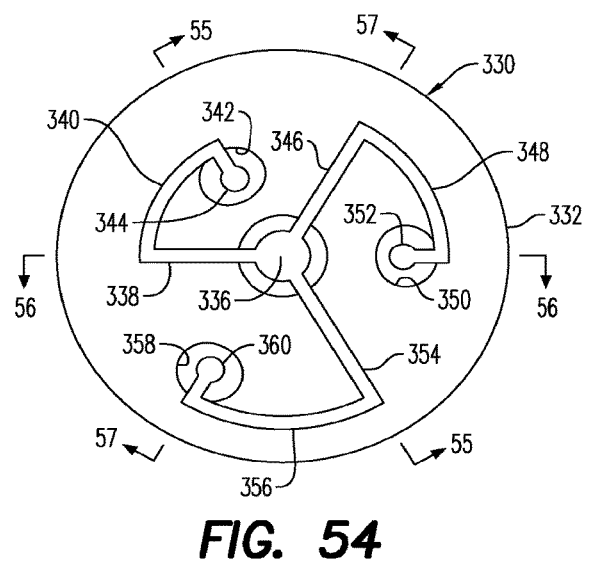
FIG. 54

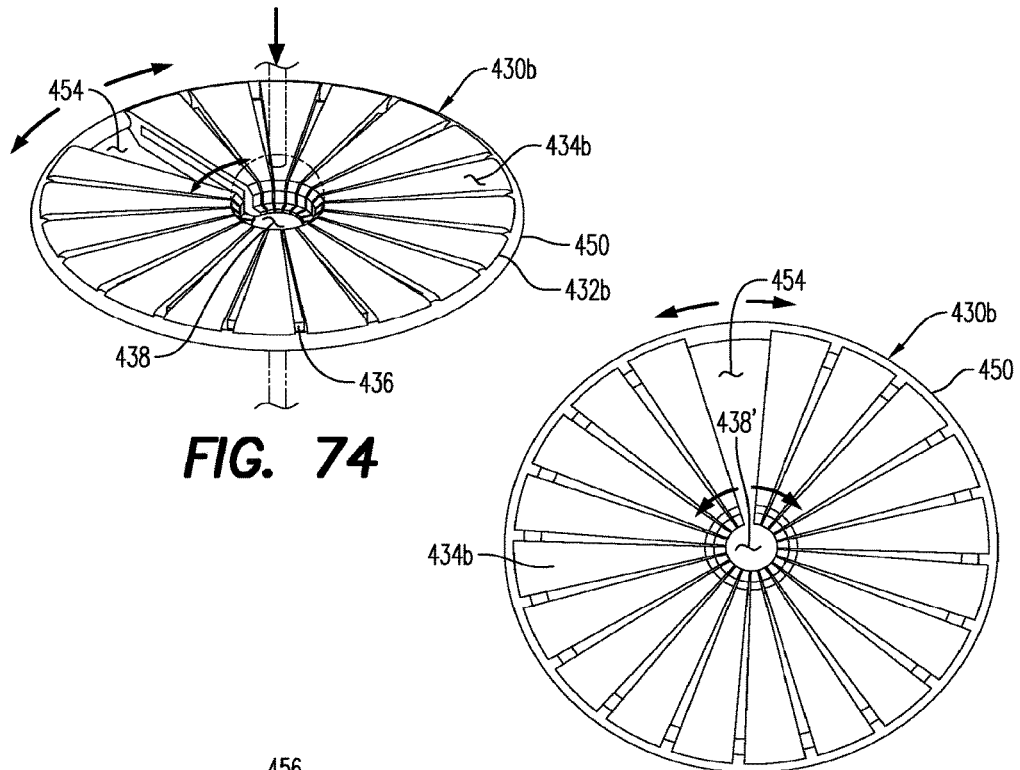
FIG. 74
FIG. 75
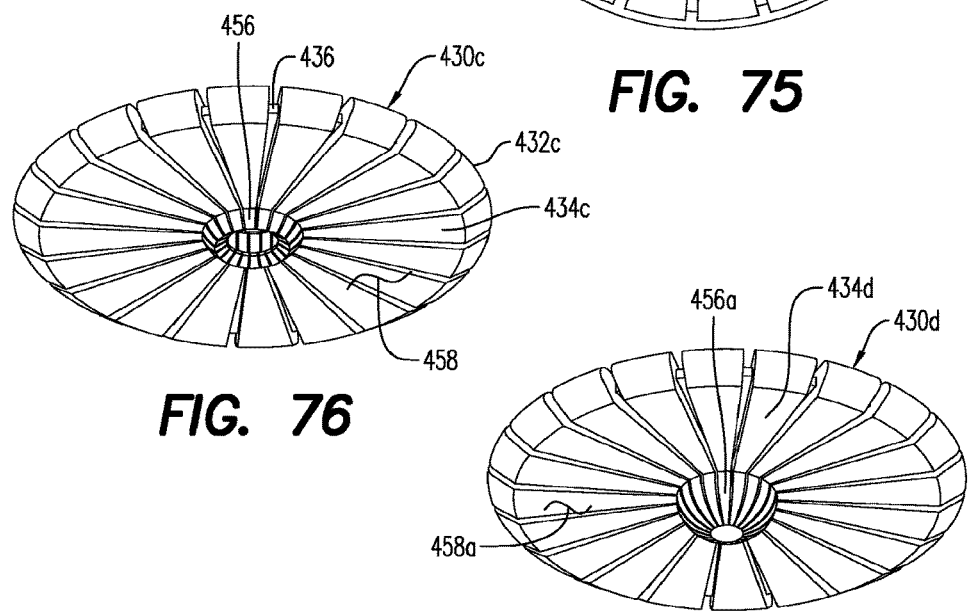
FIG. 76
FIG. 76A

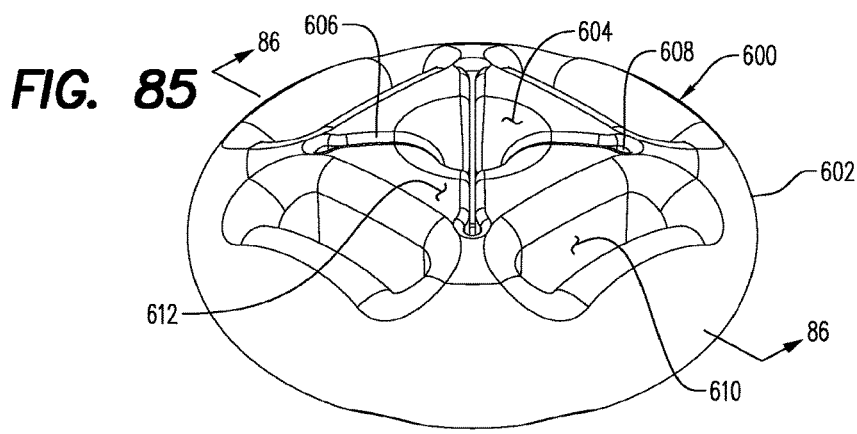
FIG. 85
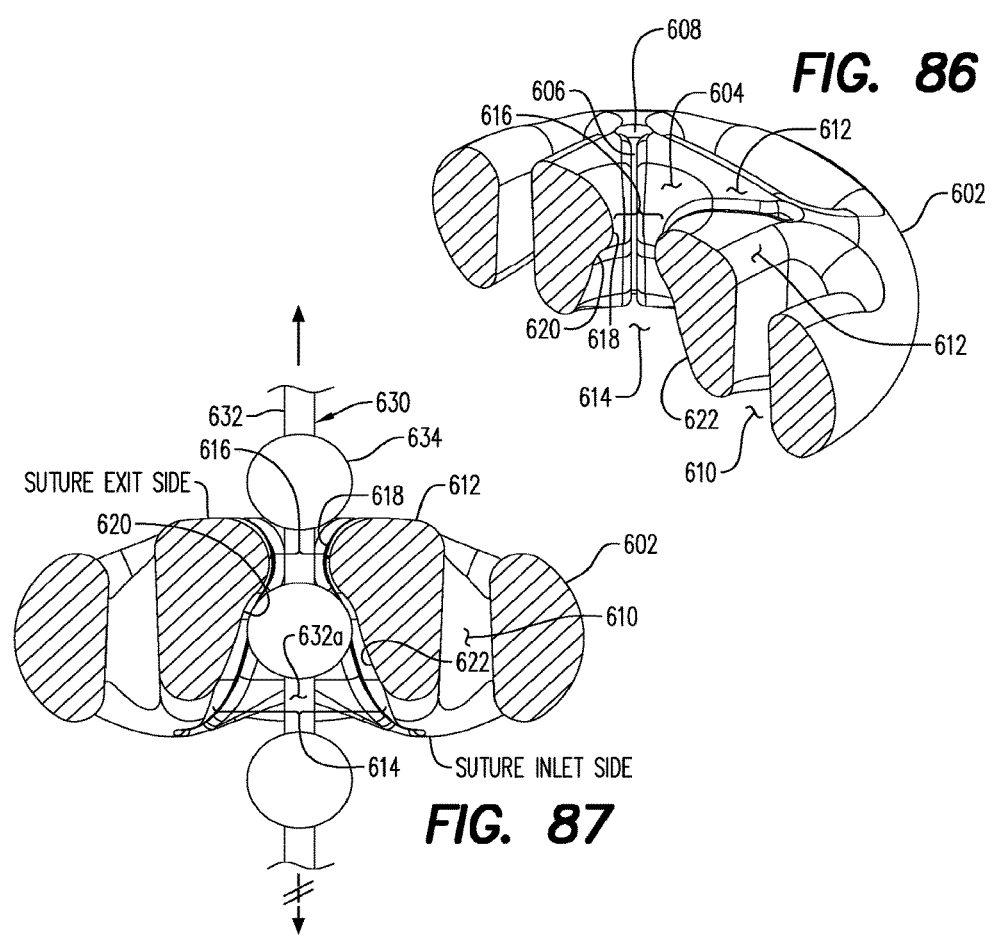
FIG. 86
FIG. 87

SURGICAL SUTURE SYSTEM, TISSUE RESTRAINTS, AND TISSUE ANCHORS

BACKGROUND OF THE INVENTION

Field of the Invention

This invention relates generally to surgical apparatus and methods for repair of torn tissue, and more particularly to a system, components thereof, and method for arthroscopic and other surgical repair of torn tissue and tissue reattachment by providing the system for suturing and anchoring the torn tissue together against other tissue substrates, or for attaching tissue to medical, veterinary and dental implants.

Description of the Related Art

The rotator cuff is composed of four tendons that blend together to help stabilize and move the shoulder. When a tear occurs in the rotator cuff of the shoulder, it is often necessary to reattach the torn tendon or tendons to the bone of the humeral head. In a common prior art rotator cuff reattachment technique, the torn cuff is punctured by a punch, and prethreaded suture anchor screws (soft tissue fasteners) are drilled into the head of the humerus bone and the sutures threaded through the anchor screws are passed through the cuff in a difficult procedure using suture relay devices to pass the sutures through the tissue. After the suture strands are passed through the tissue, they are knotted and tied together to secure the reattached rotator cuff to the humerus head (knotted-technique). Other types of prior art suture anchors are cylindrically shaped members that are pressed into holes drilled into the bone and engage the cancellous mass surrounding the drilled hole and apply friction to hold the suture in place.

Many anchor/suture devices require knots to be tied, which is difficult with minimally invasive surgery and having a "knotless" solution is an advantage in these situations. It is desirable to have an engineered suture/capture construct that does not use friction to hold the suture in place, a technology employed and found in most of today's "knotless" tissue repair devices. Furthermore, a knotless device is desirable that does not crimp, crush, pinch or interfere with the suture with a friction type hold, which will avoid potential damage to the suture.

In my prior U.S. Pat. No. 6,491,714, an apparatus and method for arthroscopic repair of torn tissue such as a rotator cuff was taught wherein torn tissue such as a rotator cuff is positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole. A soft tissue anchor having expandable wings at its distal end and sutures secured to an eyelet at its proximal end is releasable connected to the distal end of a tubular deployment tool with the free ends of the sutures extending through the deployment tool.

The deployment tool is passed through the inner cannula and a hole is drilled until the expandable wings clear the far end of the hole, a sufficient distance to allow the wings to expand to a diameter larger than the diameter of the drilled hole. The deployment tool, inner cannula, drill guide and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

Unlike conventional soft tissues anchors which are anchored in the cancellous bone mass beneath the rear cortex of the bone, the '714 teaching in one embodiment provides a suture anchor which is engaged on the exterior of the far cortex of the bone and completely bypasses the cancellous bone mass. The cortex of the bone is much less susceptible to osteopenia than the cancellous interior of the bone. The sutures are passed through the tissue when the anchor is set, and thus the difficult procedural step and use of devices such as punches and suture relays to pass and tie the sutures through the torn tissue is eliminated.

Calibrated markings on the '714 deployment system allow for precise measurement of the far cortex and precise measurement of the depth of insertion and engagement of the anchor device on the far cortex, such that structures beyond the cortex are not violated, and the button hold-down feature eliminates the traditionally difficult arthroscopic tying techniques.

In another broader aspect of the '714 invention, the surgical apparatus includes any form of a tissue substrate anchor of a conventional well-known structure, an elongated suture member securable at its proximal end to the anchor, and a separate torn tissue retainer which lockably engages as desired along the length of the suture member. The suture member extending through the torn tissue from the anchor and the tissue substrate. The torn tissue retainer is movable along the length of the exposed portion of the suture member until it is tightly positioned against the torn tissue and automatically locked in that position by non-reversible lockable engagement with the suture member. A separate tissue gripping member formed preferably as a semiflexible plate or disc having a substantially larger surface area than the tissue retainer is also provided for enhanced retention of the torn tissue in place against the outer surface of the tissue substrate.

Still another broad aspect of this '714 invention is directed to a surgical apparatus which includes an integrally formed tissue substrate anchor having an elongated suture member formed as a unit therewith. A separate disc-shaped retainer lockingly engages with the exposed distal end of the suture portion at any desired point along the suture interlocking portion. The tissue retainer is therefore moveable along the length of the exposed engaging members of the suture member for tightening the tissue layer against the tissue substrate. Utilized another way, a tear such as that found within a torn meniscus may be reconnected utilizing this embodiment of the invention.

Currently, soft-tissue fixation products that utilize "knotless" technology and screws rely on an "interference-fit" for holding power between the screw and bone. In general, non-screw anchors have a pullout strength near 200 newtons, and screws can have upwards of 400 newtons of pullout strength.

The present disclosure allows for the introduction of a revolutionary type of surgical suture system tissue restraints and tissue anchors. Related to the original application Ser. No. 12/912,313 and furthermore following C.I.P. application Ser. No. 13/281,963, this continuation-in-part offers the final engineering of the tissue restraint/capture and defines how this system can be incorporated into medical, veterinary or dental implants of any nature, whether for tissue repair, holding tissue to an implant or for stabilizing an implant in the body.

The '963 C.I.P. introduced various improvement over the initial '313 application which were related to the tissue restraint/capture design which included, in part, various geometries that could be utilized on the entrance and exit side of the tissue restraint/capture to keep the suture from traveling in a reverse direction. This approach uses a suture with protuberances that are not deformable and the locking mechanism uses various deformations of the tissue restraint/capture. Furthermore, further suture protuberance designs were introduced that could, alone, with their specially configured protuberances, prevent reverse movement after passing through a tissue restraint/capture or in conjunction with the geometry of the tissue restraint/capture achieve this goal. In that prior approach the suture's protuberances would deform.

A revolutionary type of anchor was also introduced for soft-tissue fixation to bone, a specialized bone screw that could be utilized as a bone screw, interference screw, but, which would have the suture with its specialized deformable protuberances travel through the screws in some fashion, with the suture protuberance design preventing reverse travel through the screw. These screws were designed to optimize pull-out strength.

This present continuation-in-part introduces our latest engineering improvements in the tissue restraint/capture. While the tissue restraints/captures in the first continuation-in-part, '963 application, were deformable, allowing a suture with protuberances to pass in one direction only, we discovered that the forces needed to pull the suture through the tissue restraint would not be greatly different than the threes preventing reverse movement, i.e., either too much force was needed to pull the suture through the tissue restraint/capture or the prevention of reverse movement back through the tissue restraint/capture was too little. This latest tissue restraint/capture solves these issues with very specific parameters. In addition, this continuation-in-part describes the specific nature how this latest tissue restraint/capture can be used alone, used in multiples and can be attached to a medical, veterinary or dental implant. Based upon the present disclosure, a "pipe-line" of products will be created using knot-less, self-locking interface as a technology development platform for all types of torn medical, veterinary or dental tissue and for attaching all types of tissue to medical, veterinary or dental implants.

The foregoing examples of the related art and limitations related therewith are intended to be illustrative and not exclusive. Other limitations of the related art will become apparent to those skilled in the art upon a reading of the specification and a study of the drawings.

SUMMARY OF THE INVENTION

The present disclosure is broadly directed to a surgical suture system for tissue repair and reattachment of torn tissue to a tissue substrate found in the medical, veterinary or dental domains, medical, veterinary or dental prosthesis or medical, veterinary, dental implants. The system includes an elongated flexible suture member having a plurality of longitudinally spaced protuberances along a length thereof, and utilized in conjunction with a suture capture, which can be utilized alone or in plurality with one suture or in conjunction with any of a plurality of tissue engaging members such as suture tissue restraints, anchors, and medical, veterinary or dental implants, each including uniquely configured locking apertures sized to receive the suture member passed therethrough to allow longitudinal movement of the suture member in only one direction through the locking apertures for suture member tightening and retention. Tissue engaging anchors structured to securely receive one or more of the suture tissue restraints or suture captures either before or during a surgical procedure.

For the purposes of this disclosure, the terms "tissue restraint" or "suture capture", alone or combined as tissue restraint/suture capture means a disk-shaped device for oneway locking engagement with a flexible surgically implantable suture having spaced apart protuberances, preferably beaded. When referred to as a tissue-restraint, the device is being used to restrain tissue by the tensioning of the suture between the device and another anchor or restraint means. When referred to as a "capture", the device is being secured to a tissue implant or anchor or surgically implantable device such as a pacemaker or prosthetic for tensionable locking engagement with a suture. The term "construct" refers to the combination of a tissue restraint/suture capture, a suture, and a medical, veterinary, or dental implant wherein the tissue restrain/suture capture and the anchor or implant are independent or secured together.

The locking aperture of the tissue restrain/suture capture provides for higher resistance on the exit side of the locking aperture and lower resistance on the entrance side of the locking aperture. The suture easily passes through the entrance to the locking aperture of the tissue restrain/suture capture and leaves through the exit side of the locking aperture, both allowing the suture to travel forward in a "Go" direction. The distinct design prevents the suture from travelling in reverse or pulled backward from the entrance to the locking aperture in a "No-Go" direction. In addition, the suture cannot gravel through the locking aperture from the exit side to entrance side without complete suture failure. The purpose is to maximize the forces in the "No-Go" direction, while minimizing the forces in the "GO" direction to create as large a differential as possible. Maximizing this differential does two things; firstly, it allows the suture to easily pass through the locking aperture in the "GO" direction with minimal force which reduces or eliminates kinking or crimping of the suture. If greater forces were utilized in an attempt to repair the tissue, the force of pulling the suture through the locking aperture, might tear tissue or pull the implant away from the tissue, and secondly, maximizing the "NO-GO" forces allows the tissue restraint/capture to hold tissue with forces approaching the strength the suture itself. This disclosed technology confers at least a 1.5:1 "NO-GO", GO ratio and has approach ratios exceeding a 5:1 ratio. This design of the tissue restrain/suture capture allows these ratios to remain constant despite the size of the tissue restraint/suture capture. Sizes of 4.5 mm, 7 mm, 10 mm and 20 mm in diameter are provided, which increases the "NO-GO" and 'Go" forces, however, the ratio between these various sizes typically remaining similar an not limited to these sizes alone.

It is therefore an object of this invention to provide a surgical suture system for tissue repair and attachment of torn tissue together, to a tissue substrate or medical, veterinary or dental implant.

A broad aspect of this disclosure provides for the reattachment of any torn or damaged tissue or artificial tissue to any form of tissue substrate or together by the use of a uniquely configured tissue restrain/suture capture used alone or with other forms of tissue restraints, the tissue restraint/suture capture having a unique locking aperture arrangement for receiving a suture having spaced apart protuberances along the length of the suture. The tissue restrain/suture capture is configured for movement of the suture itself through the locking aperture in only one direction so that any tightening movement of the suture within the tissue restrain/suture capture is locked from reverse movement therebetween.

The following embodiments and aspects thereof are described and illustrated in conjunction with systems, tools and methods which are meant to be exemplary and illustrative and not limiting in scope. In various embodiments one or more of the above described problems have been reduced or eliminated while other embodiments are directed to other improvements. In addition to the exemplary aspects and embodiments described above, further aspects and embodiments will become apparent by reference to the drawings and by study of the following descriptions.

BRIEF DESCRIPTION OF THE DRAWINGS

FIG. 2 is a perspective view of a suture anchor configured in accordance with this disclosure.

FIG. 3 is a side elevation view of FIG. 2.

FIG. 4 is a section view in the direction of arrows 4-4 in FIG. 3.

FIG. 4A is a section view similar to FIG. 4 depicting an alternate embodiment thereof.

FIG. 5 is a perspective view of another alternate embodiment of the suture anchor of FIG. 2.

FIG. 5A is a section view in the direction of arrows 5A-5A in FIG. 5.

FIG. 11 is a simplified pictorial view of one aspect of the invention utilized to repair and restrain a broken distal phalanx of a finger metacarpal.

FIG. 12 is an elevation view utilizing another aspect of the present invention to repair torn ACL tissue of a knee joint.

FIG. 13 is an elevation view utilizing another aspect of the present invention to repair a torn MCL of a knee joint.

FIG. 18 is a side elevation view depicting another aspect of the invention for reattaching the proximal biceps tendon to the humeral head.

FIG. 19 is a simplified section view depicting another aspect of the invention for repairing a tear in the joint capsule which surrounds a shoulder socket.

FIG. 20 is an enlargement of area 20 in FIG. 19.

FIG. 24 is a simplified side elevation view showing another aspect of the invention utilized to effect a coracoclavicular ligament repair.

FIG. 25 is an elevation view utilizing another aspect of the invention to effect a subscapularis-to-humeral head repair.

FIG. 26 is a section view in the direction of arrows 26-26 in FIG. 25.

FIG. 53 is a perspective view of another embodiment of a suture tissue restraint.

FIG. 53A is a view of FIG. 53 depicting alternate positions of suture 10 engaged therein.

FIG. 54 is a top plan view of FIG. 53.

FIG. 74 is a perspective view of an alternate embodiment of FIG. 71.

FIG. 75 is a top plan view of FIG. 74.

FIGS. 76 and 76A are perspective views of alternate embodiments of the suture tissue restraint shown in FIG. 68.

FIG. 85 is a perspective view of a preferred embodiment of a tissue restrain/suture capture.

FIG. 86 is a perspective section view of the tissue restraint of FIG. 85.

FIG. 87 is a sectional view of FIG. 86 showing a beaded suture 630 secured within the tissue restraint 600.

Figure 1:
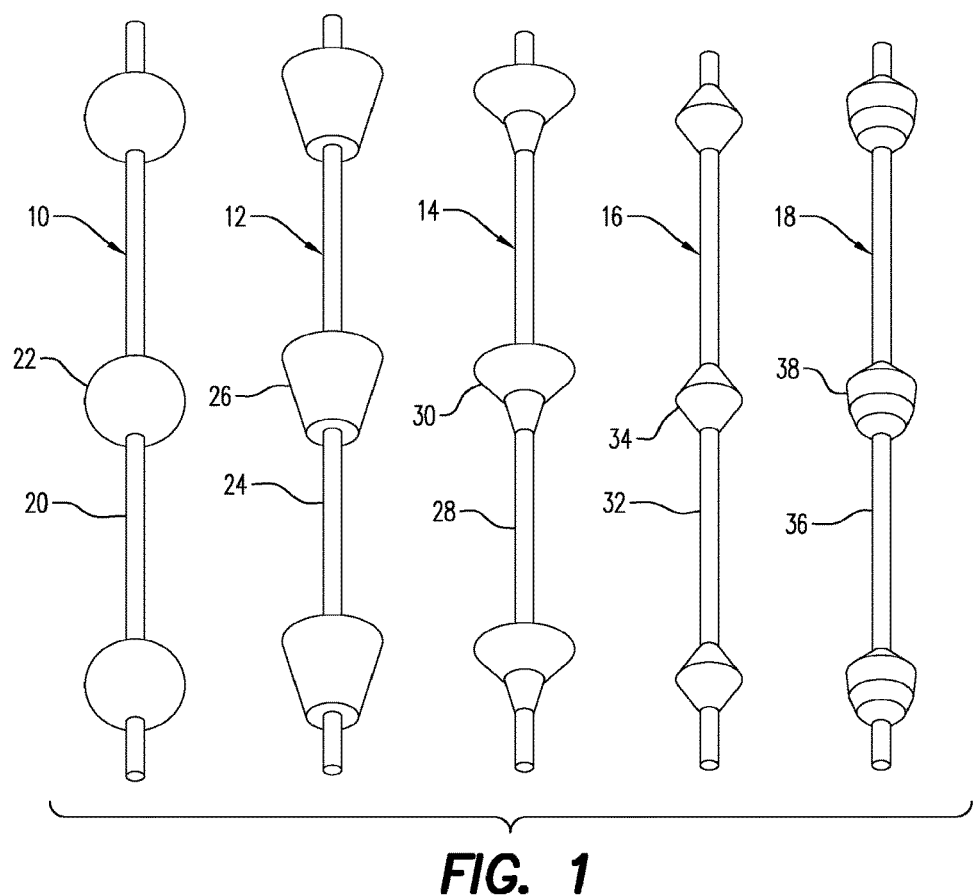
FIG. 1 is a perspective of a plurality of exemplary configurations of sutures each having spaced apart locking protuberances.

Exemplary embodiments are illustrated in reference figures of the drawings. It is intended that the embodiments and figures disclosed herein are to be considered to be illustrative rather than limiting.

DETAILED DISCUSSION

Nomenclature 10. suture
12. suture
14. suture
16. suture
18. suture
20. suture strand
22. bead-shaped protruberance
24. suture strand
26. truncated conical protuberance
28. suture strand
30. two-step conical protuberance
32. suture strand
34. symmetric conical protuberance
36. suture strand
38. segmented bullet-shaped protuberance
40. tissue anchor
41. tissue anchor
42. conical anchor body
43. tissue anchor
44. conical anchor body
45. suture entry cavity
46. suture engagement bar
47. suture exit cavity
48. suture locking aperture
49. suture one-way restriction
50. anchor post
51. suture anchor
52. anchor post cavity
53. suture entry aperture
54. tissue anchor top surface
55. suture exit aperture
56. suture tissue restraint
57. suture transverse passage
58. suture locking aperture
59. tissue gripping member
60. suture one-way lock
61. tissue anchor
62. tissue contact surface
63. tissue engaging member
64. suture severance point
65. suture locking aperture
66. suture tissue restraint
67. suture tissue restraint
68. suture locking aperture
69. aperture bevel
70. suture engagement bar
71. suture clearance aperture
72. tissue contact surface
74. open outer surface
76. tissue gripping member 78. suture clearance aperture
80. suture
82. suture strand
84. suture bare strand segment
86. hip prosthesis
88. suture locking aperture
96. orthopedic plate
98. anchor screw holes
100. suture locking aperture
102. tissue gripping member
104. suture clearance aperture
106. suture loop lock
108. suture locking aperture
110. grooved suture
112. suture tissue restraint
114. locking groove
116. groove locking edge
118. groove ramped edge
120. body
122. suture locking aperture
124. locking protuberance
126. locking edge
128. ramped edge
130. tissue anchor
132. tapered spiral thread
134. head
136. tissue penetrating tip
138. driving socket
140. suture one-way restriction
142. suture entry cavity
144 suture exit cavity
150. tissue anchor
152. tapered spiral coil
154. head
156. tissue penetrating tip
158. driving socket
160. suture one-way restriction
162. suture entry cavity
164. suture exit cavity
170. tissue anchor
172. spiral coil
174 head
176. tissue penetrating tip
178. driving socket
180. suture one-way restriction
182. suture entry cavity
184. suture exit cavity
190. tissue anchor
192. tapered spiral coil
192a-h. alternate tapered spiral coils
194. head
196. tissue penetrating tip
198. driving socket
200. suture one-way restriction
202. suture entry cavity
204. suture exit cavity
206. spiral coil segment
206a. spiral coil segment
208. tissue cutting edge
208a-g. tissue cutting edge
210. tissue anchor
212. tapered spiral coil
214. head
216. tissue penetrating tip
218. driving socket
220. Suture one-way restriction
222. suture entry cavity
224. suture exit cavity
226. centering shaft
228. tip
230. tissue anchor
230'. tissue anchor
232. tapering spiral coil
234. solid tapered screw
236. head
238. tissue penetrating tip
240. driving socket
242. suture one-way restriction
244. suture entry cavity
246. suture exit cavity
248. centering shaft
249. tip
250. tissue anchor
250'. tissue anchor
252. tapered spiral coil
254. solid tapered screw
256. head
258. tissue penetrating tip
260. driving socket
262. suture one-way restriction
264. suture entry cavity
266. suture exit cavity
268. centering shaft
270. tissue anchor
270'. tissue anchor
272. solid tapered screw
274. tapered spiral coil
276. solid tapered screw
278. head
280. tissue penetrating tip
282. driving socket
284. suture one-way restriction
286. suture entry cavity
288. suture exit cavity
289. centering shaft
290. suture
292. suture strand
294. dome-shaped protuberance
296. suture
298. suture strand
300. mushroom-shaped protuberance
302. cavity
304. suture
306. suture strand
308. cup-shaped protuberance
310. cavity
312. suture
314. suture strand
316. quarter protuberance
320. suture
322. arrow protuberance
324. arrow protuberance
326. up
330. suture tissue restraint
332. disc-shaped body
336. flexible suture passage aperture
338. radial slot
340. concentric slot
342. suture socket
344. suture strand aperture
346. radial slot
348. concentric slot
350. suture socket
352. suture strand aperture 354. radial slot
356. concentric slot
358. suture socket
360. suture strand aperture
370. suture tissue restraint
372. disc-shaped body
374. suture passage aperture
376. suture socket
378. suture strand aperture
380. radial slot
382. concentric slot
384. suture socket
386. suture strand aperture
388. concentric slot
390. suture socket
392. suture strand aperture
394. concentric slot
400. expandable suture tissue restraint
400'. expandable suture tissue restraint
402. solid segment
404. expandable suture locking aperture
406. expandable aperture segment
408. rigid aperture segment
410. suture
412. conical protuberance
414. locking surface
416. suture bearing surface
418. resilient layer
419. rigid layer
420. resilient O-ring
422. annular groove
430. expandable suture tissue restraint
430a-c. expandable suture tissue restraints
432. disc-shaped body
432'. disc-shaped body
434. rigid sector
436. resilient sector
438. expandable suture locking aperture
440. cylindrical aperture segment
442. aperture inlet segment
444. aperture outlet segment
450. resilient O-ring
452. annular groove
452'. annular groove
454. empty sector
456. tapered segment
456a. semi-spherical segment
458. tissue contact surface
460. suture/tissue restraint
462. suture
464. resilient mushroom protuberance
466. suture strand
468. suture deforming surface
470. suture locking surface
472. suture tissue restraint
474. suture aperture
476. restraint deforming surface
478. restraint locking surface
480. suture and tissue restraint
482. suture
484. resilient suture protuberance
486. suture strand
488. suture deforming surface
490. suture tissue restraint
492. suture strand aperture
494. restraint deforming surface
496. restraint locking surface
498. suture locking surface
500. suture and tissue restraint
502. suture
504. resilient suture protuberance
506. suture strand
508. suture deforming surface
510. suture locking surface
512. suture tissue restraint
514. suture aperture
516. restraint deforming surface
518. restraint locking surface
520. suture and tissue restraint
522. suture
524. resilient cone-shaped protuberance
526. suture strands
528. suture deforming surface
530. suture locking surface
532. suture tissue restraint
534. restraint deforming surface
536. suture aperture
538. restraint locking surface
540. suture and tissue restraint
542. suture
544. arrow-shaped protuberance
546. suture strand
548. suture deforming surface
550. suture tissue restraint
552. suture aperture
554. restraint deforming surface
556. suture locking surface
558. restraint locking surface
560. suture and tissue restraint
562. suture
564. arrow-shaped protuberance
566. suture strand
568. suture deforming surface
570. suture locking wake
572. suture tissue restraint
574. suture aperture
576. restraint deforming surface
578. restraint locking surface
580. tissue anchor
582. tapered spiral thread
584. tissue penetrating tip
586. head
588. suture passage
590. head deforming inlet surface
592. head locking surface
594. driving socket
600. tissue restraint/suture capture
602. body
604. suture locking aperture
606. radial slot
608. slot relief hole
610. flex arm slot
612. flex arm
614. locking aperture inlet
616. locking restriction aperture
618. reverse restriction
620. suture bead slot
622. suture bead slot approach
630. suture
632. suture strand
634. suture bead
640. tissue anchor engaged with restrain/capture 10
642. tissue anchor
644. tapered spiral thread 646. tissue penetrating tip
648. head
650. restraint receiving cavity
652. suture exist passage
654. suture entrance passage
660 tissue anchor engaged with restrain/capture 10
662. tissue anchor
664. tapered spiral thread
666. tissue penetrating tip
668. bead
670. restraint receiving cavity
672. suture clearance cavity
680. tissue anchor engaged with restrain/capture 10
682. tissue anchor
684. tapered spiral thread
686. tissue penetrating tip
688. head
690. suture passage
692. restraint receiving cavity
694. indent
695. annular groove
696. dimple
697. annular bead
700, 700'. tissue restraint/suture capture
702. body
704. suture locking aperture
706. radial slot
708. slot relief hole
710. flex arm relief hole
712. flex arm
714, 714'. suture clearance notch
716. locking aperture restriction
720, 720'. tissue anchor engaged with restrain/capture 10
722, 722'. tissue anchor
724, 724'. tapered spiral thread
726. tissue penetrating tip
728, 728'. head
730, 730'. restraint receiving cavity
732, 732'. suture clearance cavity
740. tissue anchor engaged with restrain/capture 10
742. tissue anchor
744. tapered spiral thread
746. tissue penetrating tip
748. head
750. restraint receiving cavity
752. suture clearance cavity
754. bead clearance
756. bead exit
760. tissue anchor engaged with dual restraints/captures 10
762. tissue anchor
764. tapered spiral thread
766. tissue penetrating tip
768. head
770. restraint receiving cavity
772. restraint receiving cavity
774. suture passage
780. prosthesis implant
782. restraint receiving cavity Referring now to the drawings, and firstly to FIG. 1, a number of exemplary elongated flexible sutures shown generally at numerals 10, 12, 14, 16 and 18. These sutures are preferably formed of flexible or semi-flexible medically implantable material. Each of these sutures include longitudinally spaced, enlarged-in-diameter segments or protuberances 22, 26, 30, 34 and 38 formed along the length of the corresponding slender suture strand 20, 24, 32, 38 and 36.

Suture 10 is formed having protrusions 22 which are substantially spherical or bead-shaped. Suture 12 includes the protuberances 26 which are in the form of a truncated cone, while suture 14 includes protuberances having a two-step truncated conical structure. Suture 16 includes protuberances 34 having opposing truncated conical portions forming each of the protuberances, while suture 18 has a gradual three step enlargement to each of the protuberances 38, ending in a sharply truncated conical end or tail portion thereof to interact with suture locking apertures described below.

Referring now to FIGS. 2 to 4, one embodiment of a tissue anchor within the scope of this invention is there shown generally at numeral 40 and is formed of a medically implantable material. This tissue anchor 40 includes a conical anchor body 42 having outwardly extending spiral threads which tightly lockingly engage into a tissue substrate such as bone or cartilage. As with all of the tissue anchors and suture tissue restraints disclosed within the scope of this invention, this tissue anchor 40 includes a suture engagement bar 46 having a pair of closely spaced apart suture locking apertures 48 which are sized in diameter and having one end thereof beveled so that, as will be described in detail herebelow, restrict an appropriately configured suture as described in FIG. 1 hereinabove to pass snugly through each of the suture locking apertures 48 in only direction. That is to say that the suture may be drawn into each of the suture locking apertures 48 and pulled therethrough in one direction, but reversal of movement of the suture within these suture locking apertures 48 is prohibited or substantially inhibited so as to effect a locking position in one-way movement fashion of the suture therethrough.

The suture engagement bar 46 includes an anchor post 50 which snappingly and lockingly engages into a mating anchor post cavity 52 formed into the enlarged head proximal end of the anchor body 42 so that the suture engagement bar 46 may be rotated about the longitudinal axis of the anchor body 42 relatively freely so as to quickly and easily rotationally orient the suture engagement bar 46 to a neutral tension force applied by the suture when tightened.

Referring now to FIG. 4A, an alternate embodiment of the tissue anchor 40 is there shown at numeral 40' wherein the entire suture engagement bar 46 is recessed flush with the upper enlarged top surface 54 of the anchor body 42'. Thus, once the suture has been passed through the suture locking apertures 48 after the suture engagement bar has been snappingly engaged into anchor post cavity 52' and the anchor post 50 has been thusly secured therewithin, the top or outer edge of the suture engagement bar 46 is substantially even with the enlarged top surface 54 of the tissue anchor 40'.

Referring now to FIGS. 5 and 5A, yet another embodiment of the tissue anchor is there shown generally at numeral 43. This tissue anchor 43 includes a conical anchor body 44 having outwardly extending spiral threads and a fixed transverse suture engagement bar 46' which is secured within a circular cavity formed into the head of the anchor body 44. Again, the suture engagement bar 46' includes two spaced suture locking apertures 48' each having cooperatively oriented bevels so that a selected suture will pass in only direction through the pair of suture locking apertures 48'. This embodiment 43 affords a one-piece structure with the suture engagement bar 46' secured in place and in flush alignment with the head of the anchor body 44 which is the preferred configuration of a tissue anchor of this type.

Although not shown in FIGS. 2 to 5, the head of each of the tissue anchors will be provided with tightening cavities formed into the enlarged end of the anchor body so that a separate tool my be used to drivingly engage the spiral threads into the appropriate bone or cartilage substrate. The tissue anchor 43 in FIGS. 5 and 5A may be rotationally drivingly engaged into the tissue substrate by engagement of an appropriately configured tool onto the suture engagement bar 46' which is rigidly secured in the position shown.

Figure 5B:
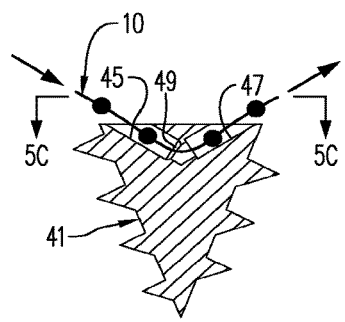
FIG. 5B is a section view of another alternate embodiment of the suture anchor of FIG. 2.
Figure 5C:
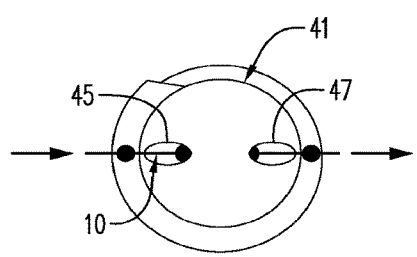
FIG. 5C is a top plan view in the direction of arrows 5C-5C in FIG. 5B.

In FIGS. 5B and C, another configuration of a tissue anchor 41 is there shown configured similarly to the tissue anchors 40, 40' and 43 previously described. However, this tissue anchor 41 includes diagonally oriented intersecting apertures 45 and 47 which converge centrally of the anchor body adjacent to the enlarged head thereof and are sized to receive and permit only one-way movement of the suture 10 in the direction of the arrows. A one-way restriction 49 is provided so as to insure that, once tightened by pulling in the direction of the arrows, the suture 10 may not be moved in the opposite direction.

Figure 5D:
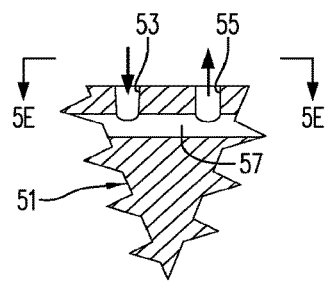
FIG. 5D is yet another alternate embodiment of the suture anchor of FIG. 2.
Figure 5E:
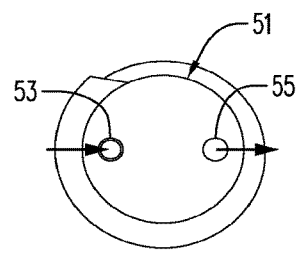
FIG. 5E is top plan view in the direction of arrows 5E-5E in FIG. 5D.

In FIGS. 5D and E, yet another tissue anchor is there shown generally at numeral 51 which also includes a pair of spaced parallel suture entry and exit apertures 53 and 55 which are interconnected by a transverse passage 57. The suture entry aperture 53 is beveled and tapered so as to facilitate only one-way movement of the suture therethrough and exiting from the suture exit aperture 55 only in the direction of the arrows shown.

Figure 6:
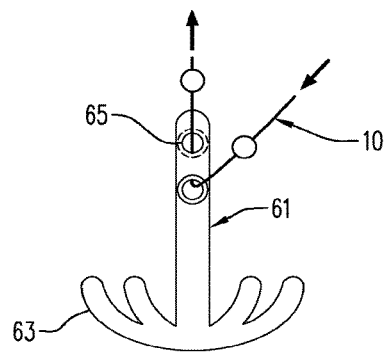
FIG. 6 is a side elevation view of another embodiment of a suture anchor of this disclosure.

Referring now to FIG. 6, another tissue anchor is there shown generally at numeral 61 formed of a medically suitable material having an elongated shank having two closely spaced apart suture locking apertures 65 formed therethrough and a plurality of circumferentially spaced radially extending tissue engaging members 63. The locking apertures 65 include oppositely oriented bevels so that the suture may be drawn through the pair of locking apertures 65 in only the direction of the arrows.

Figure 7:
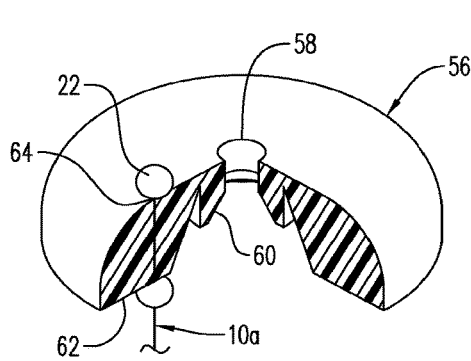
FIG. 7 is a broken perspective view of one embodiment of a suture tissue restraint.

Referring now to FIG. 7, one embodiment of a suture tissue restraint is there shown generally at numeral 56. This tissue restraint 56 may be formed of medically acceptable material. The body is domed-shaped having a flat tissue contact surface 62 and a central suture locking aperture 58 having a one-way suture lock 60 formed around the suture locking aperture 58 which prevents the suture from being drawn downwardly once a suture has been appropriately tensioned upwardly through the locking aperture 58. A second suture 10a is permanently connected through the body of the suture tissue restraint 56 extending downwardly from the flat tissue contact surface 62. However, the suture 10a may be cut at 64 and removed where a repair of tissue procedure only requires a single suture to be lockingly engaged within the suture locking aperture 58.

Figure 7A:
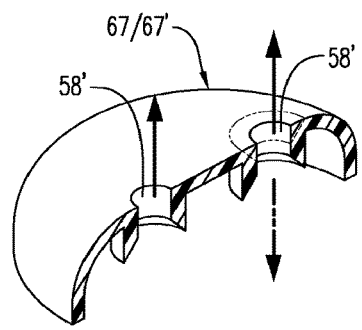
FIG. 7A is a broken perspective view of another embodiment of a suture tissue restraint.

In FIG. 7A, another suture tissue restraint is there shown generally at numeral 67 or 67' and formed having a domed-shaped body similar to that shown in FIG. 7. However, in this embodiment 67/67', two spaced apart suture locking apertures 58' are formed through the dome portion of the tissue restraint 67/67' in closely spaced relationship facing the tissue engaging side of this tissue restraint 67 so that a suture may be tensioned upwardly or away from the tissue contact surface. However, the bevels of the suture locking apertures 58' may be oriented oppositely one another to form suture tissue restraint 67' to lockingly engage a single suture for one directional movement only. Note that, if formed as shown without the missing portions, these suture tissue restraints may be snappingly engaged over a suture and they continue to function as above described.

Note that hereinbelow, tissue anchors and suture tissue restraints are sometimes collectively referred to as "tissue engaging members".

Figure 8:
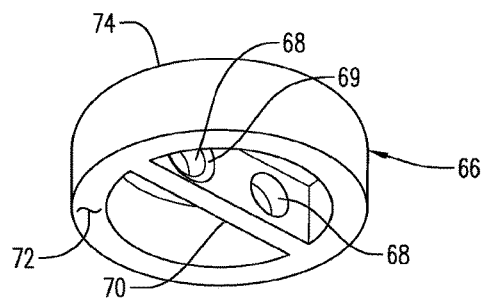
FIG. 8 is a perspective view of yet another embodiment of a tissue suture restraint.

Referring now to FIG. 8, another suture tissue restraint is there shown generally at numeral 66 having a ring-shaped body with a flat tissue contact surface 72 and an open outer surface 74. A transversely oriented suture engagement bar 70 formed as a unit with the ring-shaped body is also provided. Two spaced apart suture locking apertures 68 are oppositely beveled at 69 so as to provide the one-way locking engagement of a suture passing therethrough as previously described.

Figure 9:
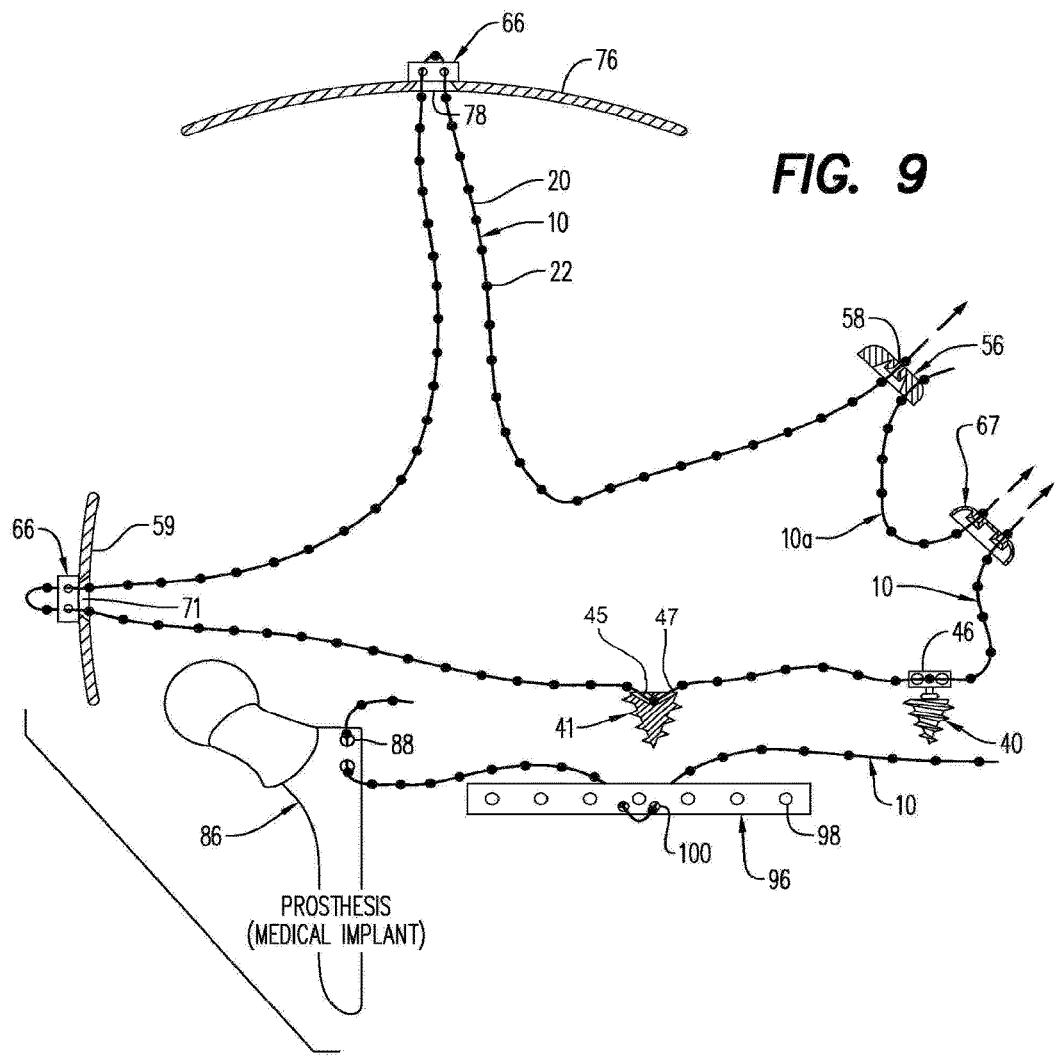
FIG. 9 is a pictorial view showing a variety of suture anchors and suture tissue restraints (absent tissue or tissue substrate for clarity) in locking engagement with one embodiment of the suture member 10 shown in FIG. 1.

Referring now to FIG. 9, a pictorial view showing a variety of tissue engaging members in relation to sutures 10 and 10a are there shown. The suture 10 is lockably engaged through the two spaced locking apertures of the suture tissue restraint 66 when positioned against a flexible tissue gripping member 59 which provides a larger tissue contact surface which will biasingly flex against the tissue or tissue substrate to maintain tension produced by the suture when suitably positioned through a suture clearance aperture 71 formed centrally through the tissue gripping member 59. Suture 10 is also shown passing through another suture clearance aperture 78 formed centrally through an enlarged tissue gripping member 76 and in one-way locking engagement with another suture tissue restraint 66.

The suture 10 also extends through the suture locking aperture of the suture tissue restraint 56 for tensioning of the suture in the direction of the arrow. The suture 10a which is permanently engaged at one end thereof into the body of the suture tissue restraint 56 as previously described then extends to one of the locking apertures of suture tissue restraint 67 while another portion suture 10 extends from the other locking aperture of the suture tissue restraint 67 for engagement through the dual locking apertures of the suture engagement bar 46 of the tissue anchor 40. This portion of suture 10 is then shown continuing on for locking engagement through suture entry and exit cavities 45 and 47 of tissue anchor 41 and then returning to the suture tissue restraint 66 through suture clearance aperture 71.

Still referring to FIG. 9, another suture 10 may also be lockingly passed through spaced locking apertures 100 formed through an elongated orthopedic plate 96 which is also provided with spaced anchor screw holes 98. Again, the spaced locking apertures 100 are cooperatively arranged and configured to allow for movement of the suture 10 in only direction therethrough. This suture 10 is shown continuing on to be lockingly engaged for one directional movement only through suture locking apertures 88 formed through a suitable portion of a typical hip prosthesis 86 or other medical implant, knee prosthesis, breast implant, cardiac pacemakers as examples but not to represent an all inclusive list, to which the suture 10 may be suitably anchored and tensioned as previously described.

Figure 10:
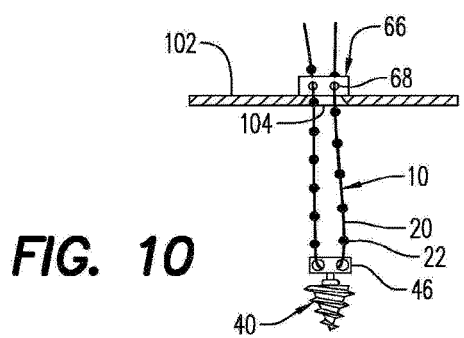
FIG. 10 is an elevation view of a typical installation arrangement of the elongated suture member 10 in locking engagement with a suture anchor 40 and a suture tissue restraint 66.

Referring now to FIG. 10, another exemplary installation arrangement utilizing the elongated suture 10 is there shown. In this embodiment, the suture 10 is passed at each end thereof through the spaced locking apertures 68 of the suture tissue restraint 66 which is positioned against a flat enlarged tissue gripping member 102 formed of thin surgical steel or other suitable material and having a suture clearance aperture 104 formed therethrough positionable in alignment with the locking apertures 68 of the suture tissue restraint 66. A mid portion of the suture 10 is lockingly engaged for one directional movement only through the suture engagement bar 46 of the tissue anchor 40 as previously described.

In FIG. 11, a pictorial view of another aspect of the invention utilized to repair and restrain a broken distal phalanx of a finger metacarpal is there depicted. The suture 10 is lockingly passed through passageways drilled or formed through the broken bone ends, a mid portion of the suture 10 passing lockingly through the spaced locking apertures of the suture tissue restraint 66, each end of the suture 10 then lockingly passed through the suture tissue restraint 67 and tensioned in the direction of the arrows to secure the fracture for healing.

In FIG. 12, repair of a torn ACL tissue of a knee joint is there depicted. The suture 10 is passed through passageways formed in the femur and the tibia in aligned opposing fashion, a mid portion of the suture passing through the spaced locking apertures of the suture tissue restraint 66 and the free ends of the suture 10 lockingly engaged through the locking apertures formed through the suture tissue restraint 67.

In FIG. 13, a torn MCL of a knee joint is shown being repaired wherein a modified suture 80 having no protuberances along one end 84 thereof is shown surgically attached to the torn end of the MCL, the suture 80 then passing through spaced locking apertures of the suture engagement bar 46 of the tissue anchor 40 which has been previously secured into the lower end of the femur.

Figure 14:
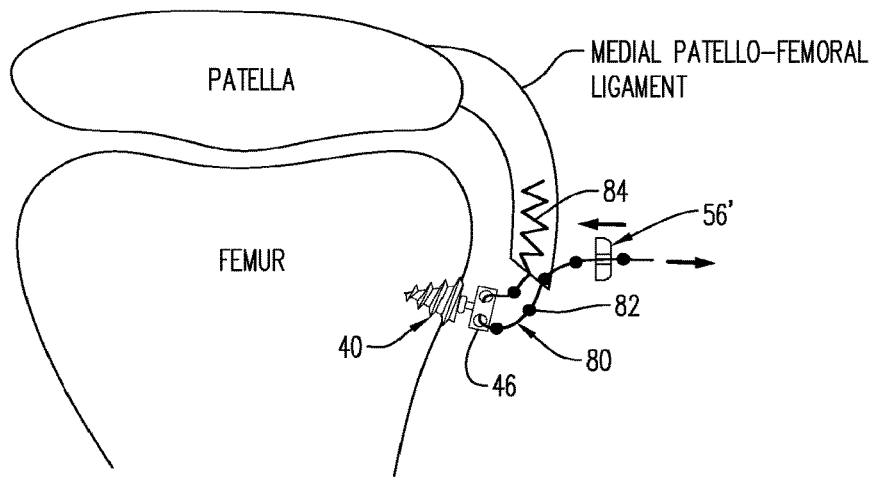
FIG. 14 is a side elevation view showing another aspect of the invention utilized to repair a torn medial patellafemoral ligament.

In FIG. 14, the repair of a torn medial patella-femoral ligament is there shown wherein one end 84 of a the suture 80 not having protuberances is surgically attached to the torn distal end of the ligament, the suture 80 then extending to the pair of locking apertures formed through the suture engagement bar 46 of tissue anchor 40 as previously described. The suture 80 then extends to the distal tip of the torn ligament passing therethrough and being secured in position by a suture tissue restraint 56', for added reattaching strength. The suture tissue restraint 56' is as previously described in FIG. 7 wherein the proximal protuberance 22 of suture 10*a* has been cleaved or cut at 64 and removed as being unnecessary.

Figure 15:
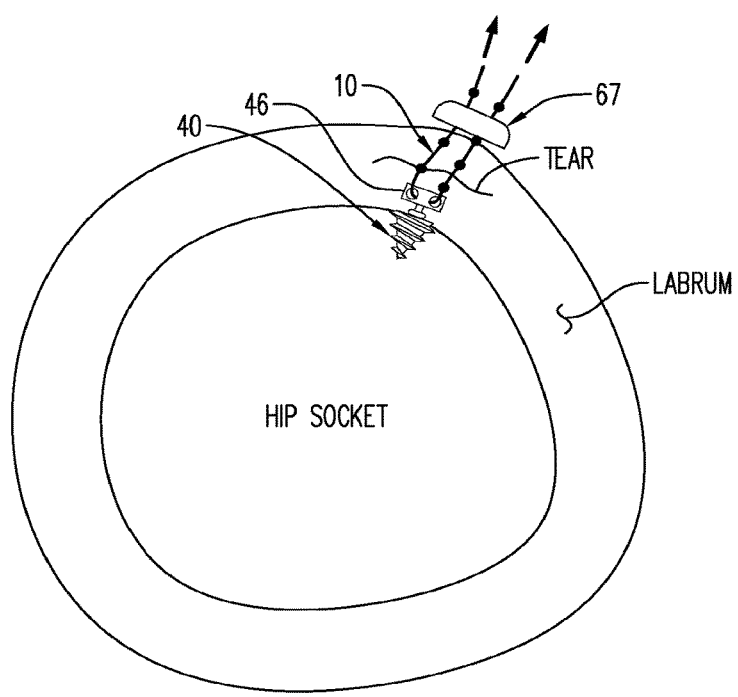
FIG. 15 is a simplified section view showing another aspect of the invention utilized to repair a tear in the hip labrum.

The repair of a tear in a labrum surrounding a hip socket is shown in FIG. 15. The suture 10 is passed through the locking apertures of the suture engagement bar 46 of tissue anchor 40 which has previously been secured into the hip socket. The suture 10 is then passed through the tear and through the locking apertures of the surgical tissue restraint 67 and tensioned in the direction of the arrows to tighten and repair the tear.

Figure 16:
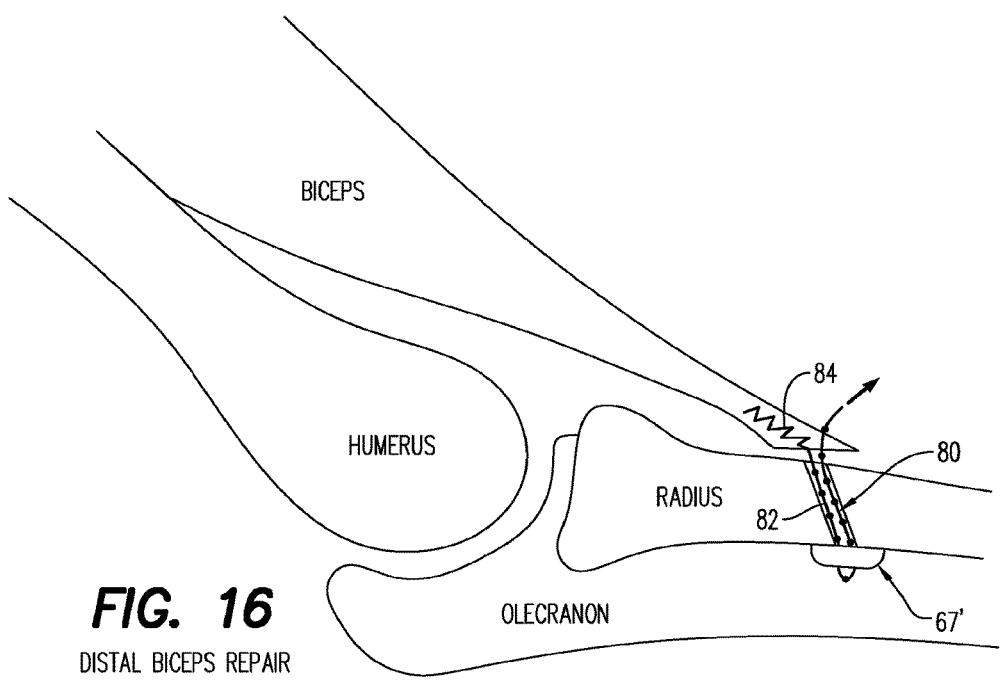
FIG. 16 depicts another aspect of the invention utilized to reattach the torn distal end of the biceps.

In FIG. 16, the repair of a distal biceps which has become detached is there shown. A modified suture 80 which is absent protuberances at one end thereof at 84 is surgically attached to the distal end of the biceps and then passed through a passageway drilled through the radius and then lockingly engaged through the locking apertures formed through the suture tissue restraint 67'. The free end of the suture 80 may be then passed back through the passageway and through the distal biceps and tensioned in the direction of the arrow to re-secure the biceps for healing.

Figure 17:
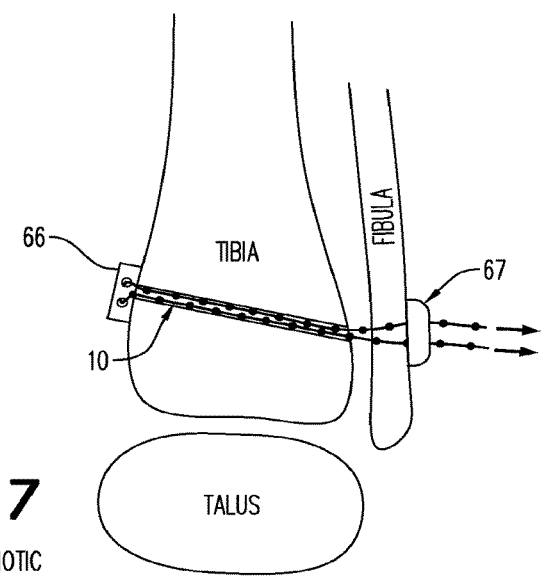
FIG. 17 shows a schematic view utilizing another aspect of the invention to reattach the fibula of an ankle syndesmotic disruption.

Reattachment of the fibula in an ankle syndesmodic disruption is shown in FIG. 17. The suture 10 is passed through a drilled transverse passageway adjacent the end of the tibia. A mid portion of the suture 10 is lockingly engaged through the locking apertures of the suture tissue restraint 66 pressed against the tibia. Another suture tissue restraint 67 then receives both ends of the suture 10 after being passed through the lower end of the fibula and tensioned in the direction of the arrows to secure the repair.

Reattachment of the proximal biceps tendon is shown in FIG. 18 wherein a modified suture 80 absent protuberances along a mid portion thereof is wrapped around the proximal biceps tendon and there secured. The protuberance-carrying ends of the suture 80 are passed through the locking passageways of two spaced apart tissue anchors 41, each of which have been previously surgically anchored into the humeral head. The ends of the suture 80 are then tensioned in the direction of the arrows to secure the repair.

In FIGS. 19 and 20, a disc-shaped suture loop lock 106 is provided with spaced apart locking apertures 108 to secure the crisscrossed ends of each suture 10 which is initially passed around the tear formed through the capsule around a shoulder socket. This repair is notably accomplished without the typical tissue anchors, relying upon the tension locking features of each of the suture loop locks 106 as shown in FIG. 20.

Figure 21:
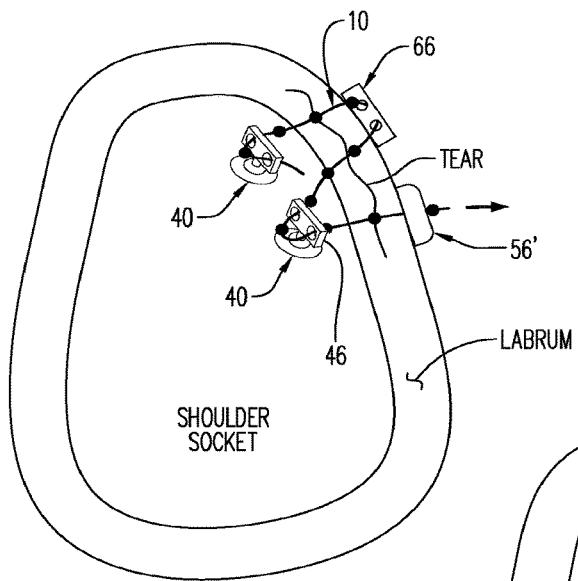
FIGS. 21 to 23 show other aspects of the invention utilized to repair a tear in the shoulder labrum surrounding a shoulder socket.
Figure 22:
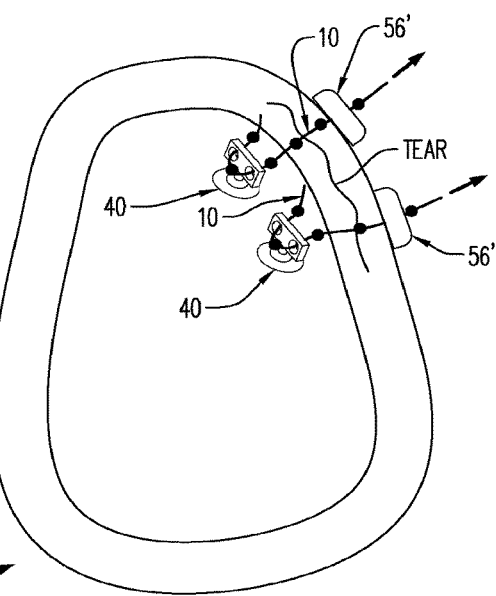
Figure 23:
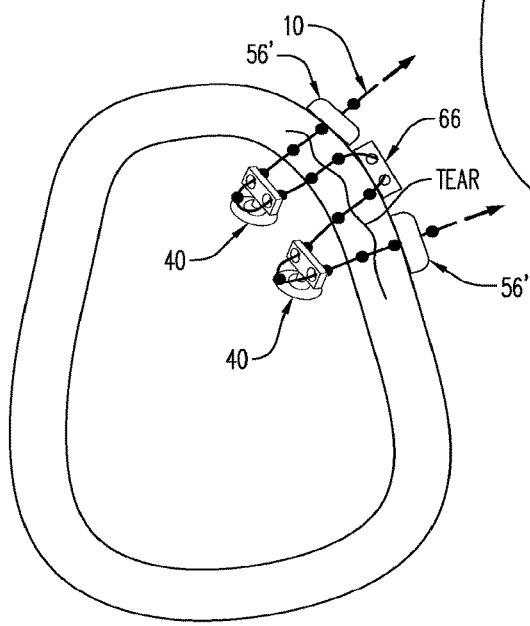

FIGS. 21, 22 and 23 show alternate repair techniques utilizing the invention to repair a tear in the shoulder labrum. FIG. 21 provides a total of three separate segments of suture 10 passing therethrough while in FIG. 22, only two separate lengths of sutures 10 are provided. However, in FIG. 23 a total of four segments of two sutures 10 more tightly draw the tear together for repair.

Repair of a detached coracoclavicular ligament is shown in FIG. 24 which utilizes two separate sutures 10 each passing through drilled passageways formed through the clavicle and the coracoid as shown. The ends of each of the suture 10 are secured through modified suture tissue restraints 56' as previously described. Tensioning of all four ends of the sutures 10 provide for both strength and refined tension adjustment of the repair.

In FIGS. 25 and 26, the repair of a subscapularis detachment is there shown wherein two sutures 10 each pass through a passageway formed through the humeral bead with modified suture tissue restraints 56' restraining each end of each of the sutures 10 as previously described.

Figure 27:
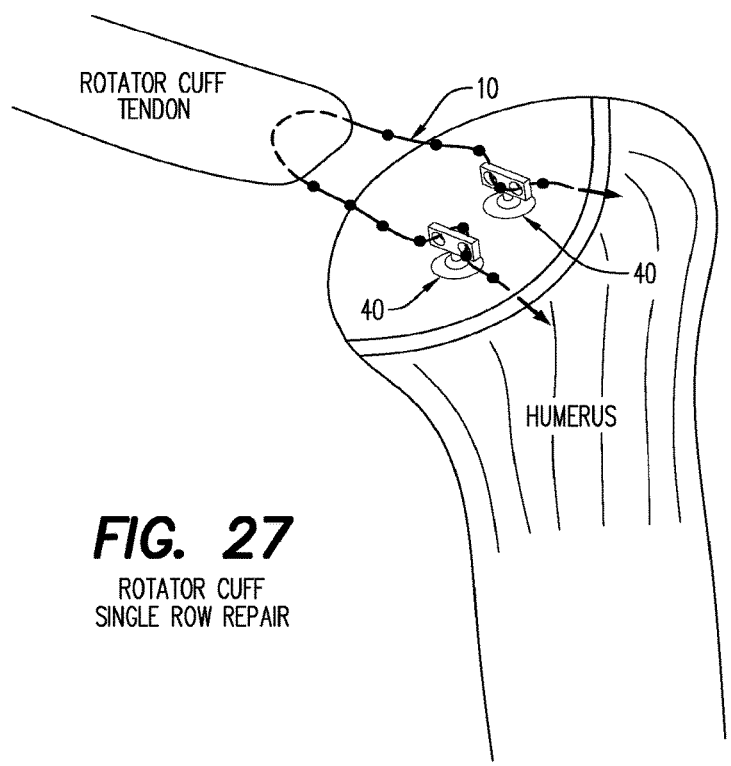
FIG. 27 is an elevation view showing another aspect of the invention utilized to reattach a rotator cuff tendon to the top of the humerus.
Figure 28:
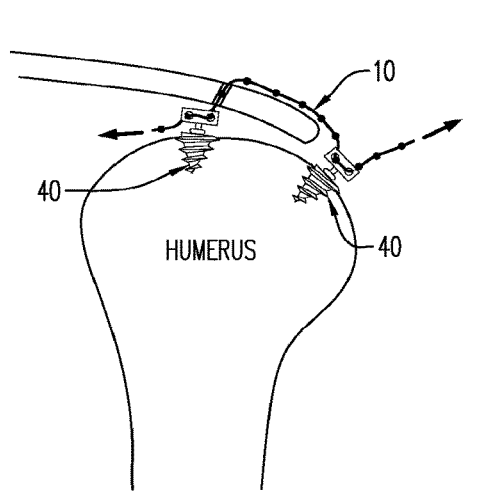
FIG. 28 and FIG. 29 depict alternate aspects of the invention utilized to effect the repair shown in FIG. 27.
Figure 29:
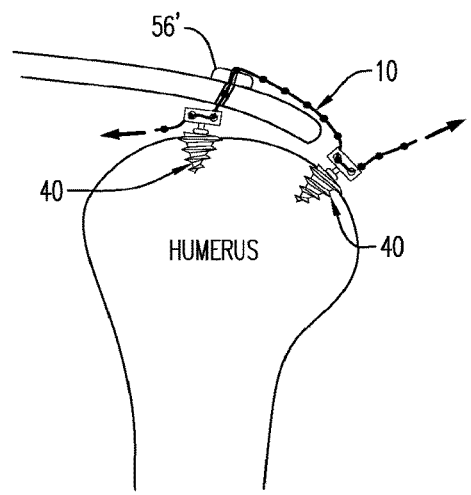

The attachment of a torn rotator cuff tendon is shown in FIG. 27 utilizing a single suture row technique. The suture 10 is passed at each end thereof through the locking apertures of each tissue anchor 40 which have been previously secured into the ends of the humerus. The suture 10 which has been previously passed through the rotator cuff tendon and tensioned at each end thereof in the direction of the arrows. In FIGS. 28 and 29, a double row repair of the rotator cuff tendon is there shown where two parallel sutures 10 are each passed through tissue anchors 40 and through the rotator cuff tendon as shown. In FIG. 29, an additional locking and retaining function against the rotator cuff tendon is provided by a modified suture tissue restraint 56'.

Figure 30:
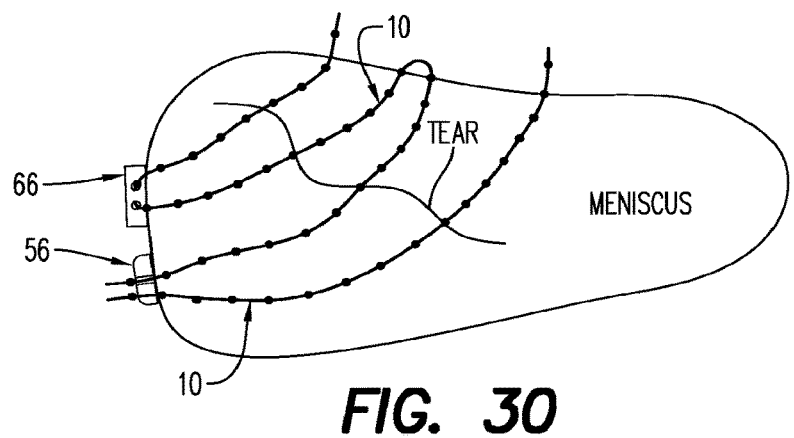
FIGS. 30 and 31 depict sagittal views depicting alternate aspects of the invention utilized to effect a meniscus tear repair.
Figure 31:
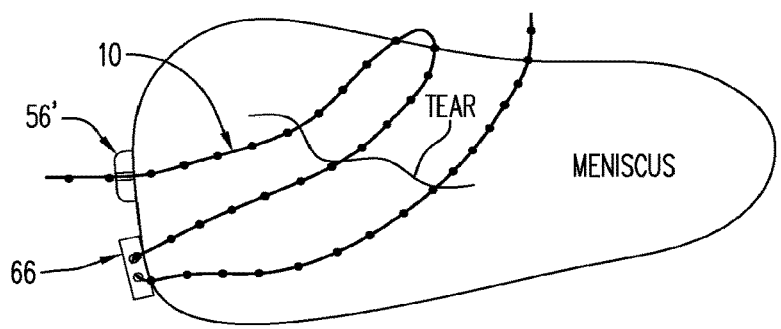

Meniscus repair is demonstrated by the use of the invention in FIGS. 30 and 31. In FIG. 30, the meniscal tear is longer requiring a total of four suture segments therethrough using two separate sutures 10. One of the sutures 10 is passed three times through the tear and anchored at a mid-portion thereof through suture tissue restraint 66 and permanently at one end thereof within suture tissue restraint 56. The permanently secured suture 10 of the suture tissue restraint 56 is then passed through the repair, exiting the opposite surface of the meniscus as shown.

Figure 32:
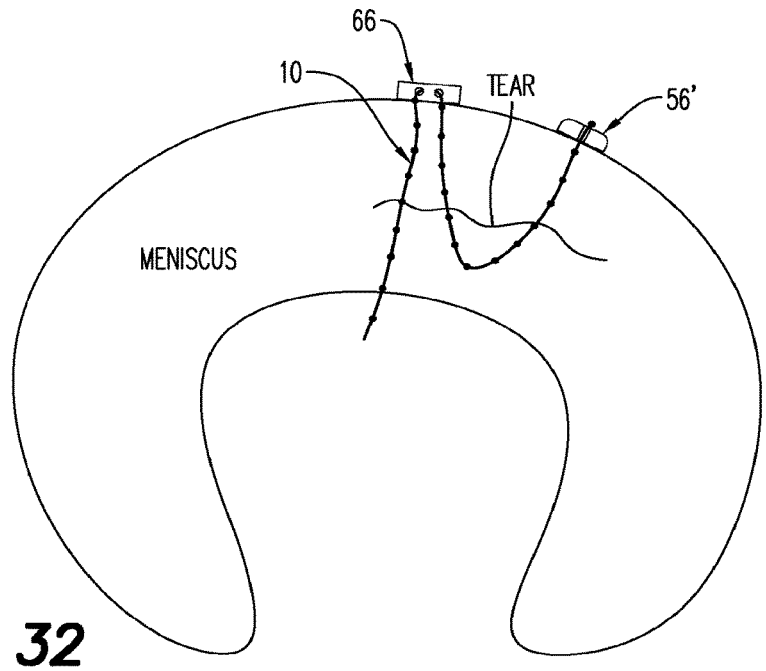
FIGS. 32 and 33 depict alternate aspects of the invention utilized to effect a torn meniscal repair.
Figure 33:
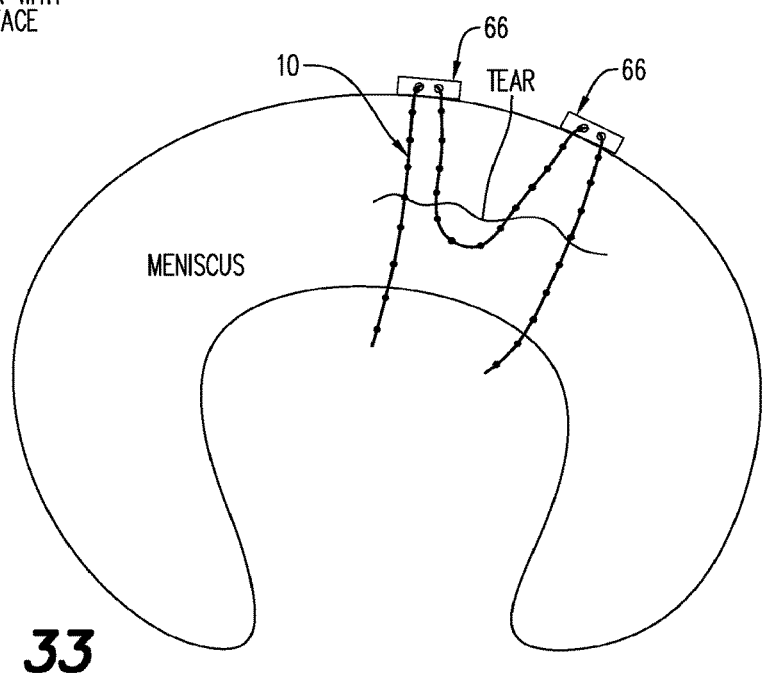

In FIGS. 32 and 33, an alternate technique for meniscal tear repair is there shown wherein, in FIG. 32, a single suture 10 is passed three times through the tear utilizing the suture tissue restraints 66 and 56' as shown. In FIG. 33, a total of four passes through the tear is provided wherein the free ends of the suture 10 are drawn from the torn meniscus without the need for suture restraint.

Figure 34:
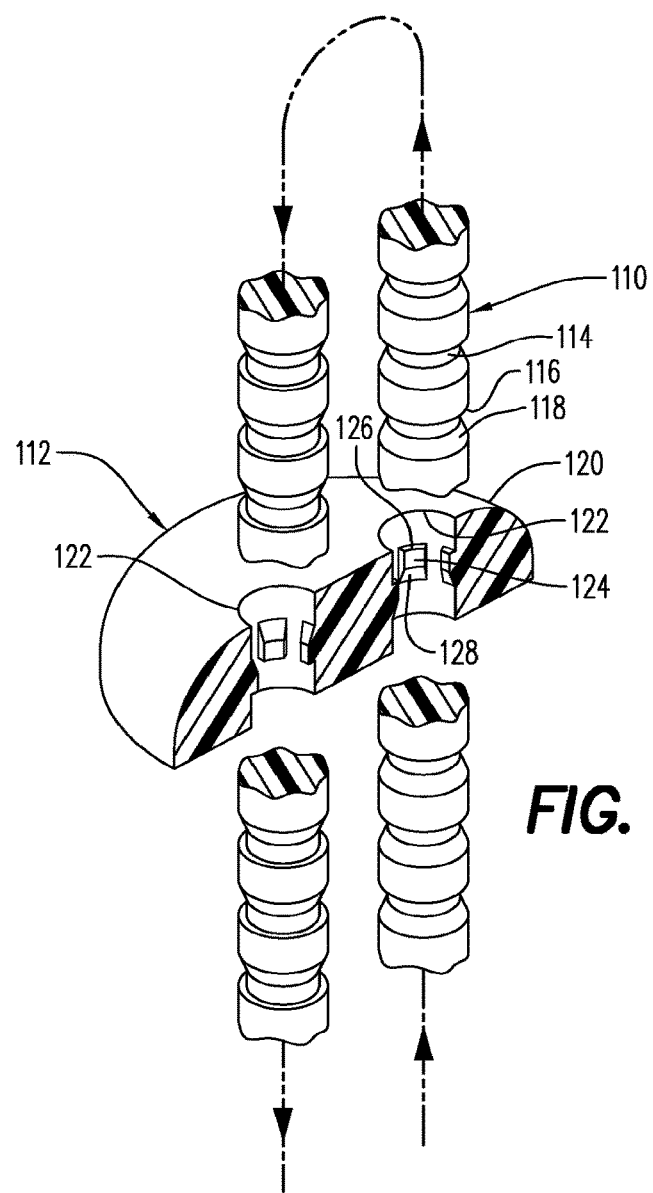
FIG. 34 is a broken perspective view of another embodiment of a suture operatively engaged with cooperatively structured suture tissue restraint.

Referring now to FIG. 34, reversal of locking protuberances and apertures is there demonstrated to be within the broad scope of this invention. Flexible elongated suture 110 is shown lockingly engaged for one-directional movement only within a pair of closely spaced locking apertures 122 of a suture tissue restraint 112. The suture has a series of spaced locking grooves formed therein which have a locking edge 116 and a ramped edge 118. Each of these grooves 114 are matingly engageable with radially inwardly extending protuberances 124 each having a square locking edge 126 and a ramped edge 128 to accomplish unidirectional movement of the suture 110.

Figure 35:
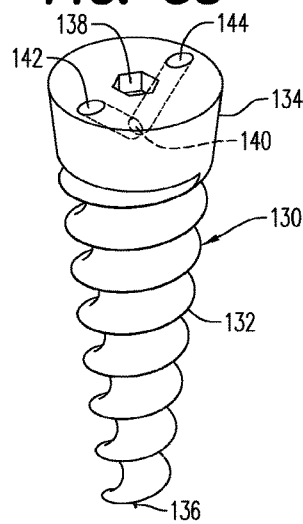
FIGS. 35 to 38 are perspective views of other embodiments of a suture anchor.

Referring now to FIGS. 35 to 47, a number of alternate embodiments of the tissue anchor are there shown. In FIG. 35, this tissue anchor 130 is formed thereof having a solid tapered spiral thread 132 with a tissue-penetrating tip 136 at the distal end. A solid tapered head 134 includes a coaxial driving socket 138 at the proximal end of this tissue anchor 130. The head 134 also includes two intersecting suture entry and exit cavities 142 and 144 having a suture restriction 140 therebetween to insure that, once a suture is pulled through these cavities 142 and 144, it may not be removed by pulling in the opposite direction.

Figure 36:
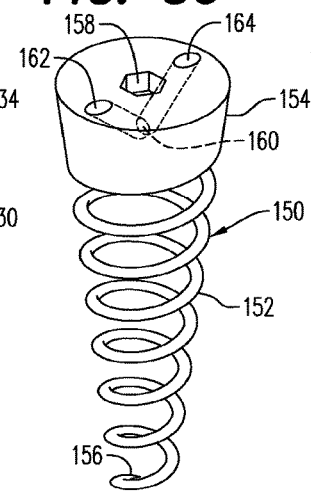

In FIG. 36, another tissue anchor 150 includes a solid head 154 and a hollow tapered spiral coil 152 extending therefrom. This coil 152 is formed of surgical stainless steel wire, spiral wound and having a sharpened tissue-penetrating tip 156 at the distal end thereof. Being hollow, less tissue is displaced as the spiral coil 152 is driven into tissue, particularly bone and tendons. Intersecting suture entry and exit cavities 162 and 164, separated by a suture one-way restriction 160, function as previously described in FIG. 35 for one-way insertion of a suture in accordance with this teaching.

Figure 37:
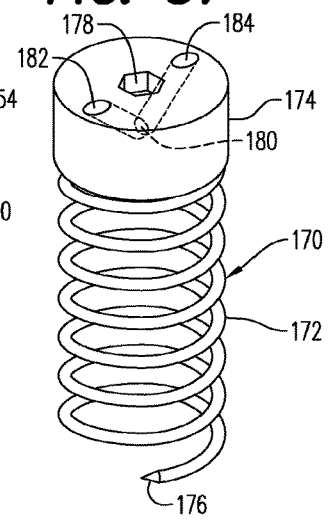

FIG. 37 discloses yet another tissue anchor 170 having a hollow cylindrically wound spiral coil 172 formed of surgical steel wire with a sharpened tissue penetrating tip 176 at its distal end. The head 174 includes an axially aligned driving socket 178 and intersecting suture entry and exit cavities 182 and 184 with a one way restriction 180 therebetween.

Figure 38:
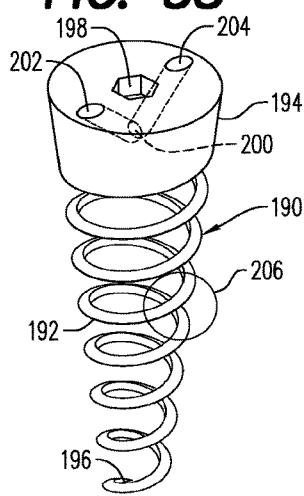
Figure 39:
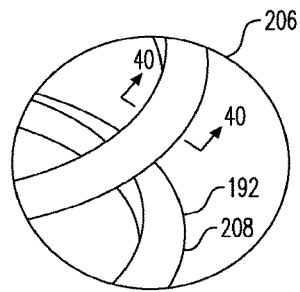
FIG. 39 is an enlarged view of area 206 of FIG. 38.

Another tissue anchor 190 is shown in FIG. 38 having a hollow tapered spiral coil 192 again with a tissue penetrating tip 196 at its distal end. The opposite end of the tapered spiral coil 192 is anchored into head 194 having a coaxial driving socket 198 at its proximal end. Suture entry and exit cavities 202 and 204 are separated within the head 194 by a suture one way restriction 200. As best seen in FIG. 39, the outer edge 208 of the tapered spiral coil 192 is sharpened for enhanced tissue cutting and securement of the spiral coil 192 as its is driven into both soft and hard tissue for enhanced permanent anchoring thereof within the tissue.

Figure 39A:
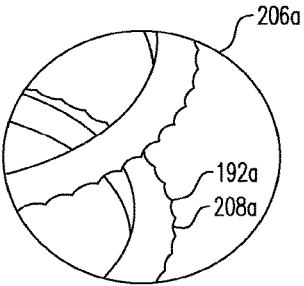
FIG. 39A is an alternate embodiment of area 206 in FIG. 39.
Figure 40:
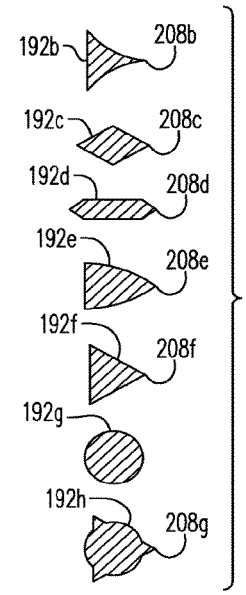
FIG. 40 shows several alternate cross-sections in the direction of arrows 40-40 in FIG. 39.

As seen in FIG. 39A, one form of outer edge enhancement is in the form of a serrated edge 208a. in FIG. 40, several alternate embodiments of the cross section of the spiral coil 192b, c, d, e, f, g, h include tissue cutting outer edges at 208b, c, d, e, f, g.

Figure 41:
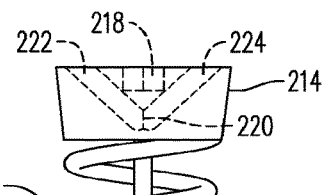
FIGS. 41 to 47 are each side elevation views of other embodiments of suture anchors.
Figures 42, 43, 44:
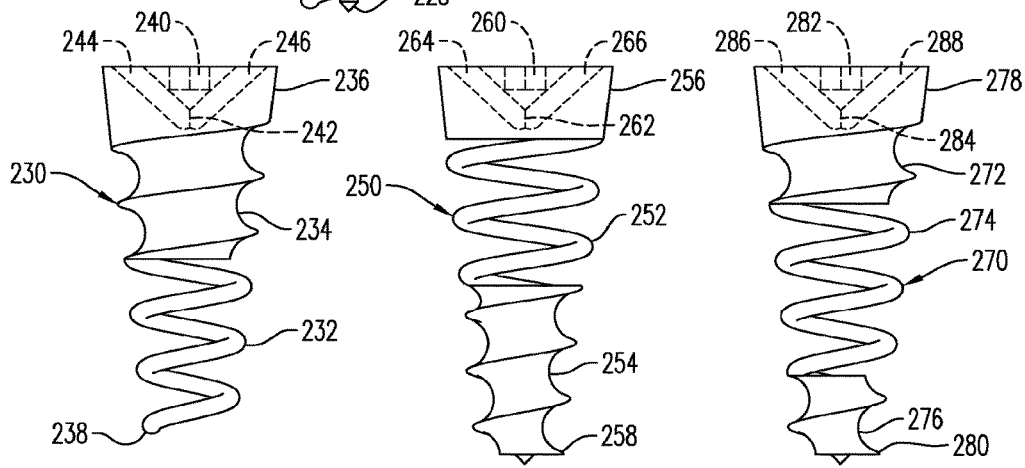
Figures 45, 46, 47:
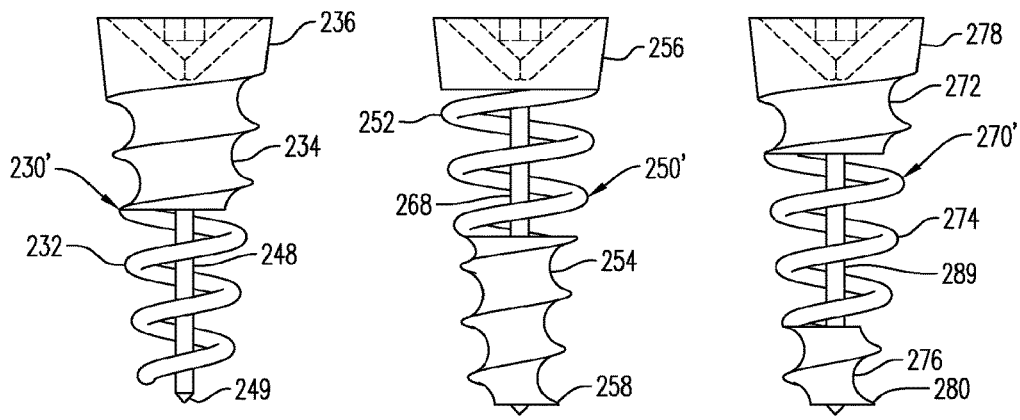
Figures 48, 49, 50, 51:
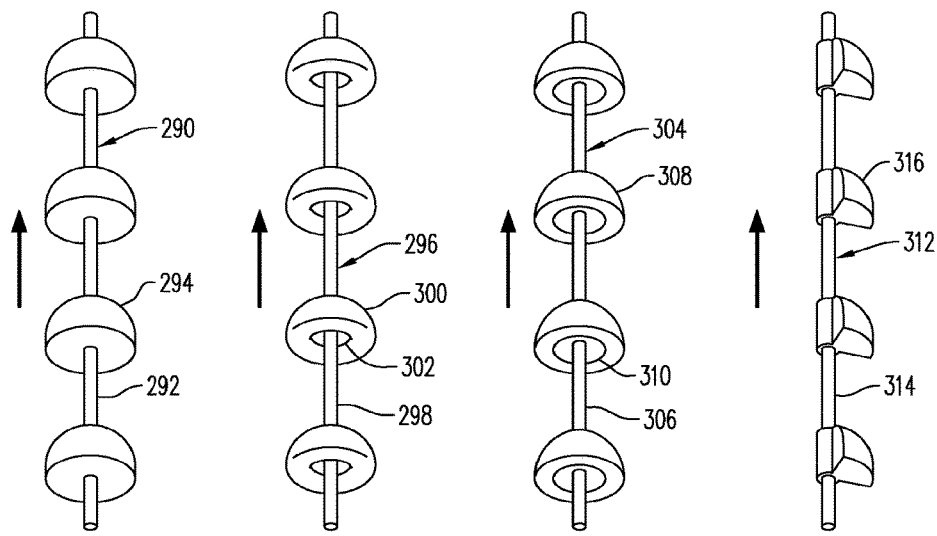
FIGS. 48 to 52 are perspective views of additional exemplary configurations of sutures.

In FIG. 41, another tissue anchor is shown at 210 also having a hollow tapered spiral coil 212 with a sharpened distal tissue-penetrating tip 216. The opposite end of the coil 212 is secured into the solid head 214. Also secured within the head 214 is a coaxial cylindrical centering shaft 226 having a sharpened tip 228 which serves to center the tissue anchor 210 as it is being rotationally driven into tissue by a suitable power unit engaged into driving socket 218. Once anchored into the tissue, a suture is passed through the intersecting suture entry and exit cavities 222 and 224, the suture being permitted only one way movement therethrough by a suture one way restriction 220 therebetween.

Additional embodiments of the tissue anchor shown in FIGS. 42 to 47 generally at 230, 250, 270, 230', 250', and 270' all include combinations of tapered tissue penetrating segments in the form of tapered spiral coils 232, 252 and 274 and solid tapered screw segments 234, 254 and 276. Each suture embodiment also includes a distal tissue penetrating tip 238, 258 or 280. Each of the solid heads 236, 256 and 278 have a driving socket 240, 260 and 282 which coaxially extend from the proximal end thereof. Intersecting suture entry and exit cavity pairs 244/246, 264/266 and 286/288 are each separated for only one way suture movement therethrough by suture one way restrictions 242, 262 and 284, respectively, as previously described. The embodiments 230', 250' and 270' in FIGS. 45, 46 and 47 also include coaxially aligned centering shafts 248, 268, and 289. Centering shaft has a pointed distal tip 249 which serves to center the tissue anchor 230' during driven rotation into tissue. Centering shafts 269 and 289 are present for stabilization and added strength between the head 256 and 278 and the screw segments 254 and 276.

Figure 52:
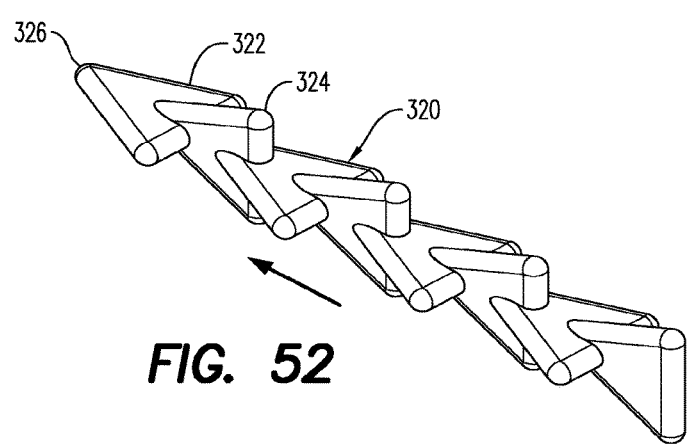

A variety of exemplary additional embodiments of the suture are shown in FIGS. 48 to 52 at 290, 296, 304, 312 and 320. Each of these suture embodiments are configured for only one way movement through appropriately configured capture arrangements formed in one or more suture tissue restraints, tissue anchors and virtually all other medical implants and devices requiring permanent securement within human tissue or bone. Each of these sutures includes an elongated flexible suture strand 292, 298, 306 and 314. Each of these sutures also includes longitudinally spaced, enlarged-in-diameter segments or protuberances 294, 300, 308, 316 and 322/324. Protuberances 294 are domed shaped, protuberances 300 are mushroom shaped having a cavity 302 formed immediately adjacent the suture strand 298, protuberances 308 are cupped-shaped also having an enlarged cavity 310 extending inwardly from the locking surface, while protuberances 316 extend around only % of the circumference of the entire strand 314 demonstrating that protuberance may be nonsymmetrical. In FIG. 52 this suture 320, absent a literal suture strand, includes spaced 90 0 offset or staggered arrow-shaped protuberances 322 and 324. A lead-in tip 326 facilitates insertion of the lead arrow 322 into tissue or the appropriately configured one-direction capture arrangement associated with various configurations of suture tissue restraints, tissue anchors and various other surgical implants and medical devices in accordance with the teaching of this disclosure.

Referring now to FIGS. 53 to 57, another uniquely configured suture tissue restraint is shown generally at 330. This tissue restraint 330 provides finer suture tension adjustability than may be available by simply tensioning the free end of the suture to the next available protuberance within other non-adjustable tissue suture restraints. This tissue suture restraint 330 includes a disk-shaped body 332. The nontissue contacting surface is generally concaved toward the central suture passage aperture 336 which is sized for free suture movement therethrough. A plurality of radial slots 338, 346 and 354 extend from the suture passage aperture 336, each being sized in width for the suture strand to freely pass therealong. The suture strand is then moved along through concentric slots 340, 348 or 356 into alignment with one of the selected suture strand apertures 344, 352 or 360. As best seen in FIG. 53A, the exemplary suture 10 may then be position so that one of its protuberances nests into a selected suture socket 342, 350 or 358.

Figure 55:
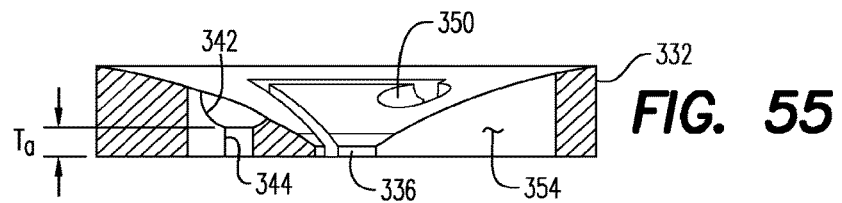
FIG. 55 is a section view in the direction of arrows 55-55 in FIG. 54.
Figure 56:
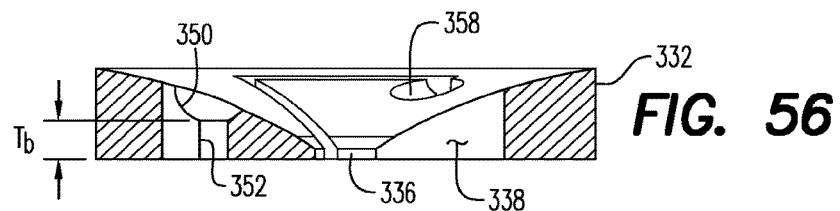
FIG. 56 is a section view in the direction of arrows 56-56 in FIG. 54.
Figure 57:
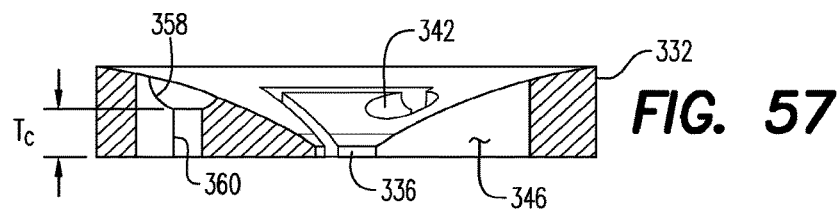
FIG. 57 is a section view in the direction of arrows 57-57 in FIG. 54.

As best seen in FIGS. 55, 56 and 57, each of these suture sockets 342, 350 and 358 are spaced from the tissue contact surface a different distance Ta, Tb and Tc which affords a much finer gradation of suture tensioning capability than normally afforded by simply pulling the suture to the next available protuberance along the length of the suture strand.

Figure 58:
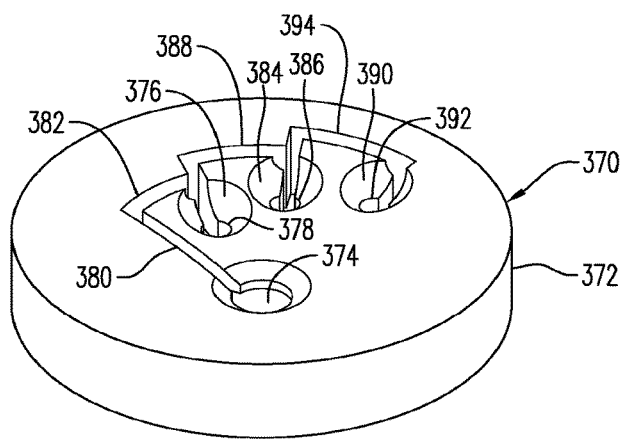
FIG. 58 is a perspective view showing an alternate embodiment of the suture tissue restraint shown in FIG. 53.

An alternate embodiment of this form of adjustable suture tissue restraint is shown in FIG. 58 at 370. This suture tissue restraint 370 includes a disk-shaped body 372 having a centrally positioned suture passage aperture 374 sized for free suture passage therethrough. However, only a single radial slot 380 is included which facilitates moving the suture strand of the suture therealong into concentric slot 382 and into alignment with suture strand aperture 378 or further along concentric slot 388 into alignment with suture strand 386 or still further along concentric slot 394 into suture strand aperture 392. The appropriate protuberance is then nestled securely into the corresponding suture socket 376, 384 or 390 in a manner similar to that shown in FIG. 53A.

Referring now to FIGS. 59 to 64, an expandable suture tissue restraint is there shown at numeral 400. This concept incorporates circumferential expandability in direction of the arrow in FIG. 59 to accommodate one-way passage of each suture protuberance through the expandable suture-locking aperture 404. This restraint 400 includes a plurality of circumferentially spaced solid segments 402 spaced apart by a series of expandable aperture segments 406. The inward tapered surfaces of these segments 402 and 406 define the tapered walls of a locking aperture 404.

Each expandable aperture segment 406 includes alternating resilient layers 418 and solid layers 419 bonded together and to the ends of the corresponding solid segments 402. As a suture 410 shown in FIG. 62 having tapered truncated conical shaped spaced saw tooth-shaped protrusions 412 is drawn through the suture locking aperture 404, the circumference of the locking aperture 404 expands in the direction of arrows 59 best seen in FIGS. 63 and 64 to allow the suture 410 to be pulled therethrough only in the direction of the arrow in FIG. 62, surfaces 416 and 418 interacting to prevent reverse movement of the suture 410.

Figure 63:
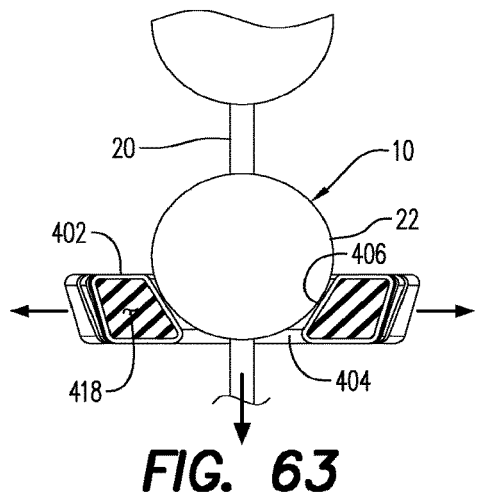
FIG. 63 is a view similar to FIG. 62 showing another suture 20 lockingly engaged therein.
Figure 64:
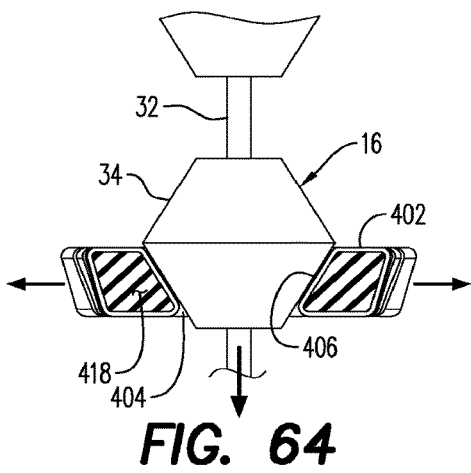
FIG. 64 is yet another view of FIG. 62 showing yet another suture 32 lockingly engaged therein.

Referring additionally to FIGS. 63 and 64, alternate configurations of the protuberance 22 and 34, respectively, will also be lockingly passable in one way fashion in the direction of the arrow causing the expansion of the resilient segments 418 as the corresponding protuberance 22 or 34 passes forcibly therethrough.

Figure 59:
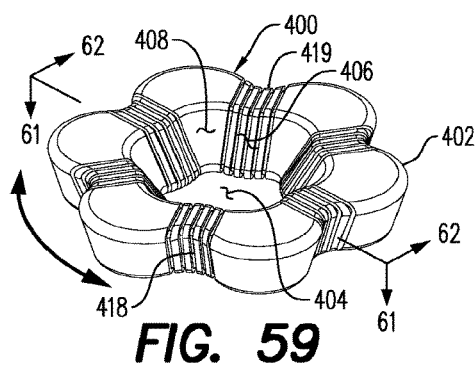
FIG. 59 is a perspective view of an expandable suture tissue restraint.
Figure 60:
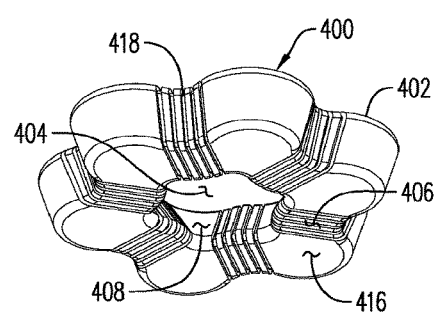
FIG. 60 is another perspective view of the suture tissue restraint shown in FIG. 59.
Figure 61:
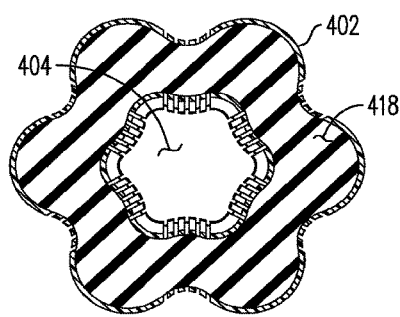
FIG. 61 is a section view in the direction of arrows 61-61 in FIG. 59.
Figure 62:
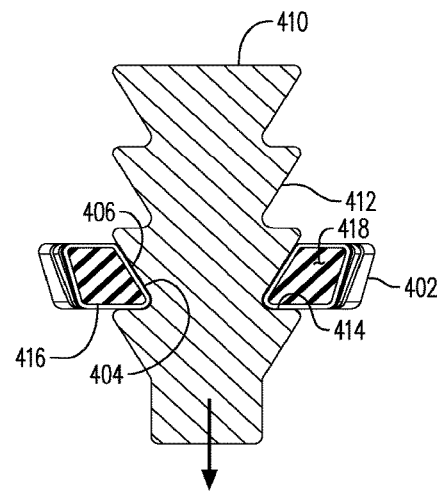
FIG. 62 is a section view in the direction of arrows 62-62 in FIG. 59 and including an interlock suture 410 therein.
Figure 65:
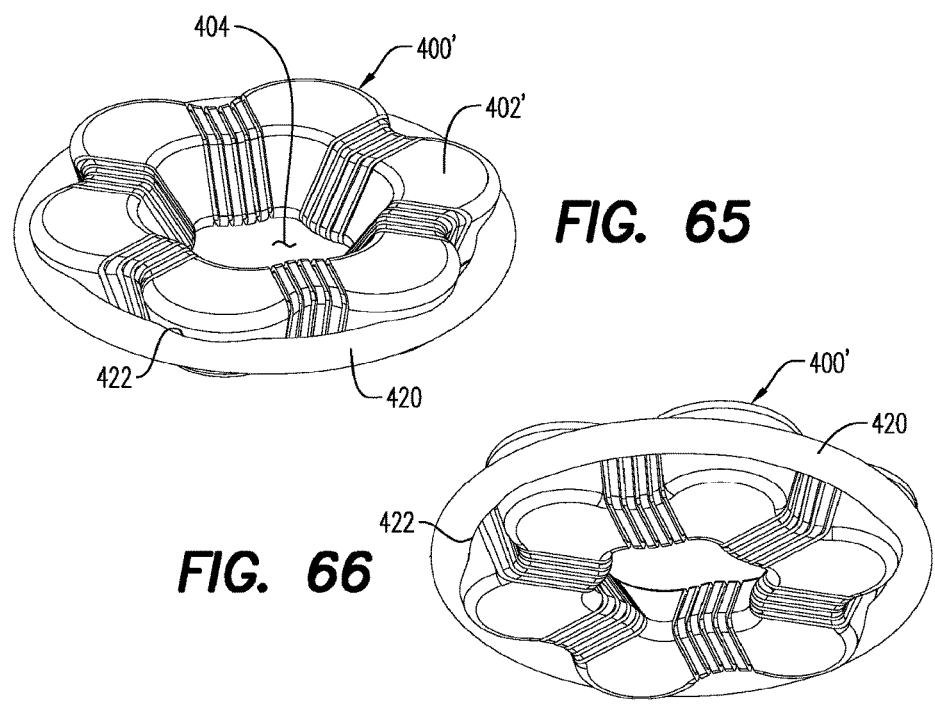
FIGS. 65 and 66 are perspective views of an alternate embodiment of the suture tissue restraint 400 shown in FIGS. 59 and 60, respectively.
Figure 66:
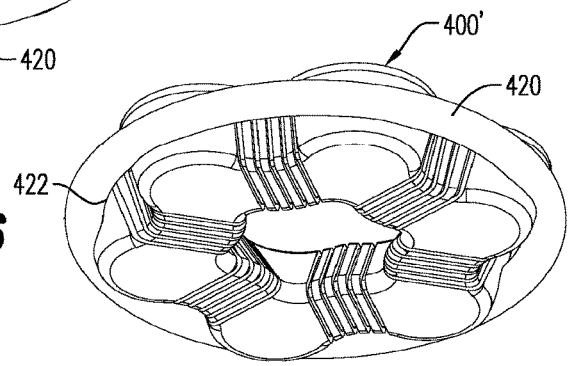

In FIGS. 65 and 66, an alternate embodiment to that shown in FIG. 59 is shown generally at numeral 400' which includes substantially the same elements of embodiment 400 except for the addition of an elastic resilient O-ring 420 tightly fitted into an annular grove 422 formed inwardly into each of the solid segments 402'. The O-ring 420 has a relaxed diameter smaller than that of the annular grove 422 such that, when stretched into place within the annular grove 422, resistance to elastically stretching the diameter of the suture-locking aperture 404 is increased.

In FIGS. 67 to 73, two embodiments of a pie-shaped expandable suture tissue restraint are there shown at 430 and 430*a*. These embodiments, 430 and 430*a*, have a generally button or disk shaped body 432 and are preferably compatible with sutures having a spherical protuberance as described above and include a plurality of spaced apart rigid sectors 434 which are separated by very thin and thus resilient flat disk 436 as best seen in FIG. 70B. Alternately, this resilient flat disk 436 may be formed of a more resilient elastomeric material. The expandable suture-locking aperture 438 is configured having cylindrical aperture segments 440 and outwardly tapered inlet aperture segments 432 configured to allow a spherical protuberance or the like of a suture to pass downwardly therethrough in the direction of the arrow in FIGS. 70A and 70B by the elastic expansion of suture-locking aperture 438. The outlet aperture segments 444 seat the spherical protuberance but will not allow it to pass back through the suture-locking aperture 438, thus locking the suture in place relative to the expandable suture restraint 430.

Figure 67:
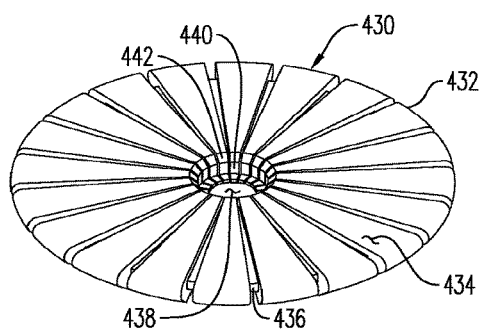
FIGS. 67 and 68 are perspective views of another embodiment of a suture tissue restraint.
Figure 68:
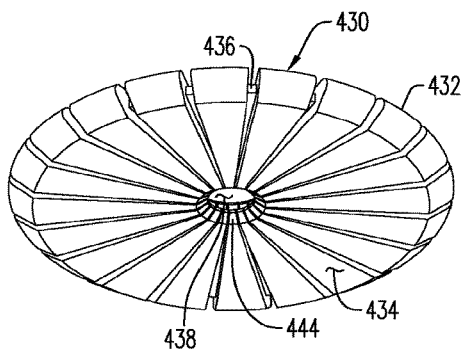
Figure 69:
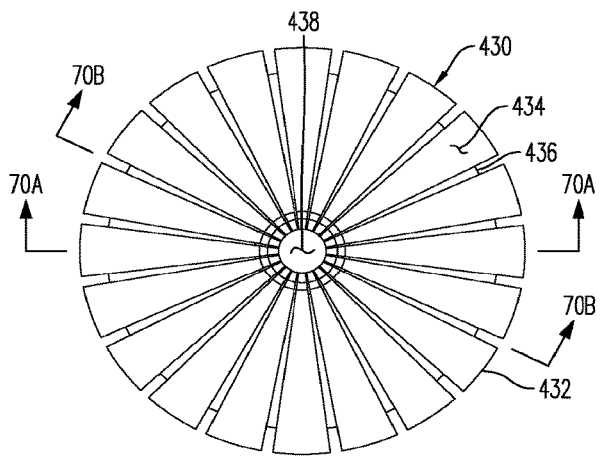
FIG. 69 is a top plan view of FIG. 67.
Figure 70A:
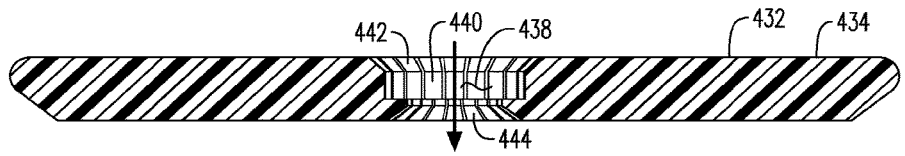
FIGS. 70A and B are section views in the direction of arrows 70A-70A and 70B70B in FIG. 69.
Figure 70B:
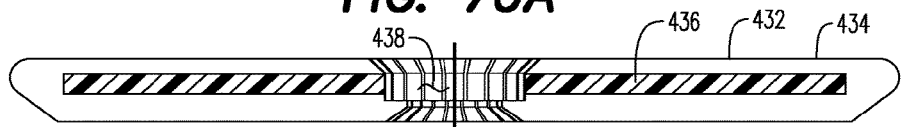
Figure 71:
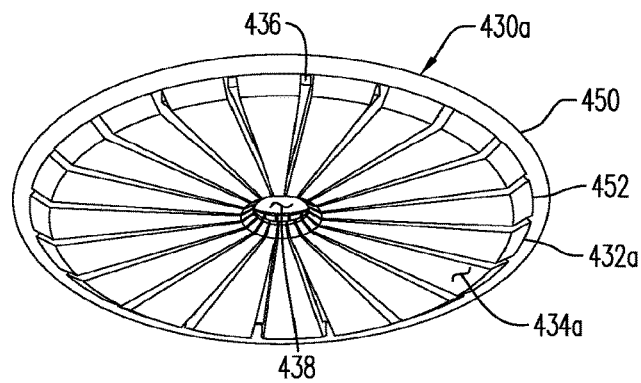
FIG. 71 is an alternate embodiment of the suture tissue restraint 430 shown in FIG. 67.
Figure 72:
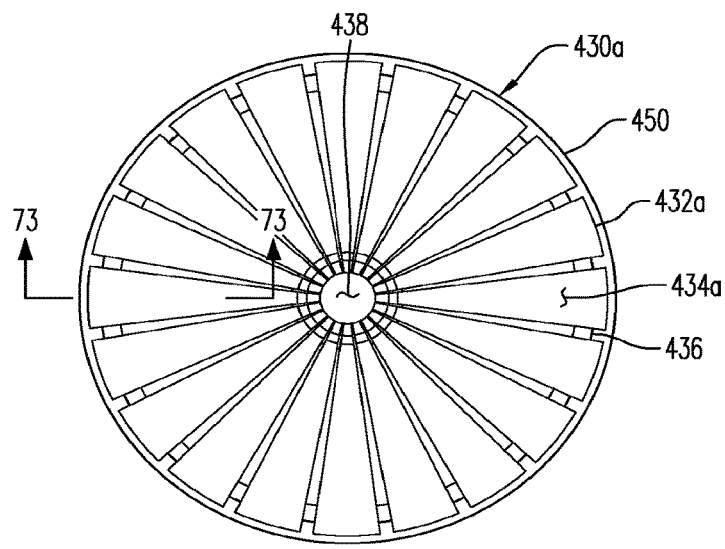
FIG. 72 is a top plan view of FIG. 71.
Figure 73:
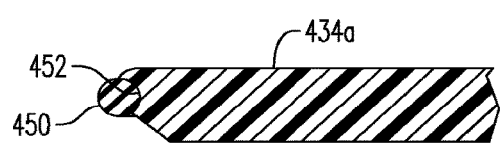
FIG. 73 is a section view in the direction of arrows 73-73 in FIG. 72.
Figure 77:
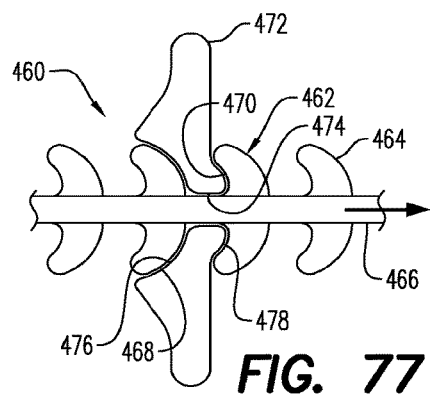
FIGS. 77 to 82 are side elevation views of alternate embodiments of additional sutures engaged within suture tissue restraints.
Figure 78:
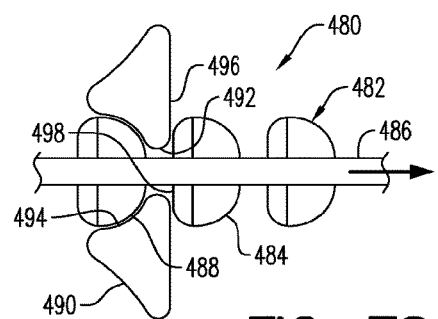
Figure 79:
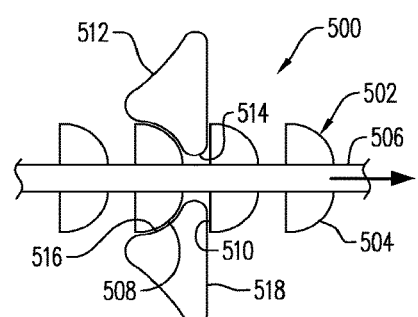
Figure 80:
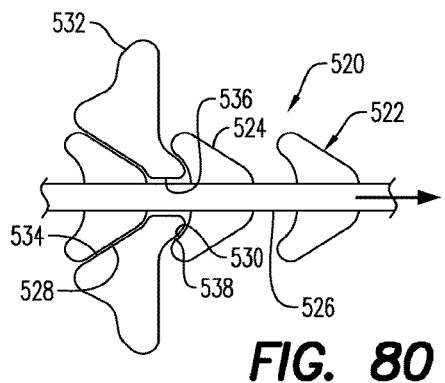
Figure 81:
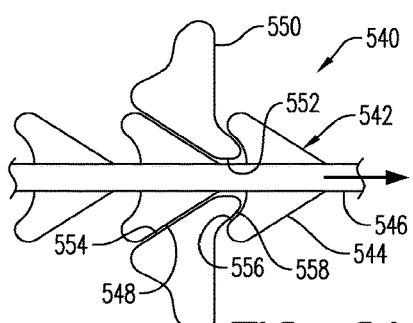
Figure 82:
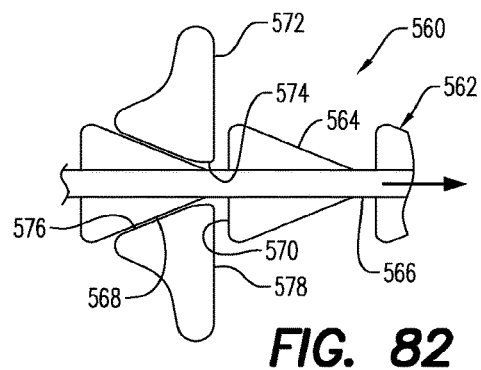

Referring additionally to FIGS. 71 and 72, an alternate embodiment to that shown in FIG. 67 is there shown at 430*a* which includes a disk-shaped body 432*a* having spaced apart rigid sectors 434*a* held together by thinner resilient disk 436 as previously described. A resilient O-ring 450 is stretchingly embedded into an annular groove 452 formed into the outer ends of each of the rigid sectors 434*a* for enhanced elasticity of the expandable suture locking aperture 438 as previously described.

Referring now to FIGS. 74 and 75, another alternate embodiment of the expandable suture restraint of FIG. 67 is there shown generally at numeral 430*b*. In this embodiment 430*b*, one of the rigid sectors 434*b* is deleted as shown at 454. All other features of this embodiment 430*b* are as described with respect to FIG. 71. This disk-shaped body thus acts as a C-shaped body and is free to elastically expand in the direction of the arrows to allow resilient enlargement of locking aperture 438 to 438' when a protuberance is forcibly urged therethrough only in the direction of the arrow.

Referring now to FIGS. 76 and 76A, two additional alternative embodiments of the expandable suture tissue restraint of FIG. 1 are there shown generally at numerals 430*c* and 430*d*. Each of these embodiments 430*c* and 430*d* provide tapered segments 456 and 456*a* of each rigid sector 434*c* and 434*d*, respectively, which collectively define a centered extension of the tissue contact surfaces 458 and 458*a* which serve to better avoid lateral movement of the suture tissue restraint 430*c* and 430*d* when embedded into soft tissue as the suture is tensioned.

Referring now to FIGS. 77 to 82, a series of suture/tissue restraint arrangements 460, 480, 500, 520, 540, and 560 including sutures 462, 482, 502, 522, 542 and 562 inserted into suture tissue restraints 472, 492, 512, 532, 550 and 572 are there shown. In these arrangements, the protuberances 464, 484, 502, 524, 544 and 564 which are attached to or formed as a part of the corresponding suture strand 466, 486, 506, 526, 546 and 566 resiliently deform as they are pulled through the respective suture apertures 474, 492, 514, 536, 552 and 574 in the direction of the corresponding arrows. The protuberances are resiliently deformed by the displacing interaction of the surfaces 468/476, 488/494, 508/516, 528/534, 548/554, and 568/576. Locking resistance to reverse direction movement of each of these sutures is achieved by the overall configuration of each of the protuberances and the mating configurations of surfaces 470/478, 498/496, 510/518, 530/538, 556/558, and 570/578.

Figure 83:
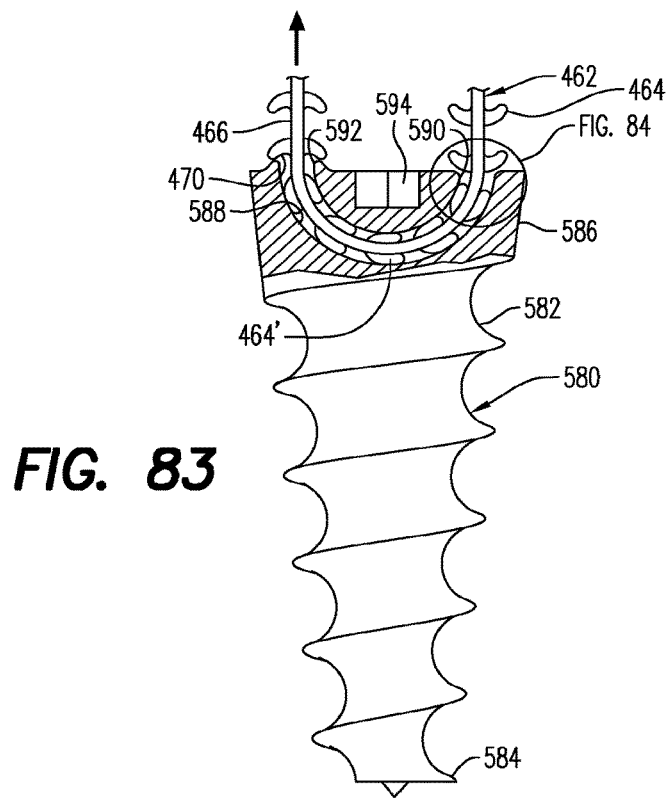
FIG. 83 is a side elevation broken view of another alternate embodiment of the tissue anchor and suture 462 of FIG. 77.
Figure 84:
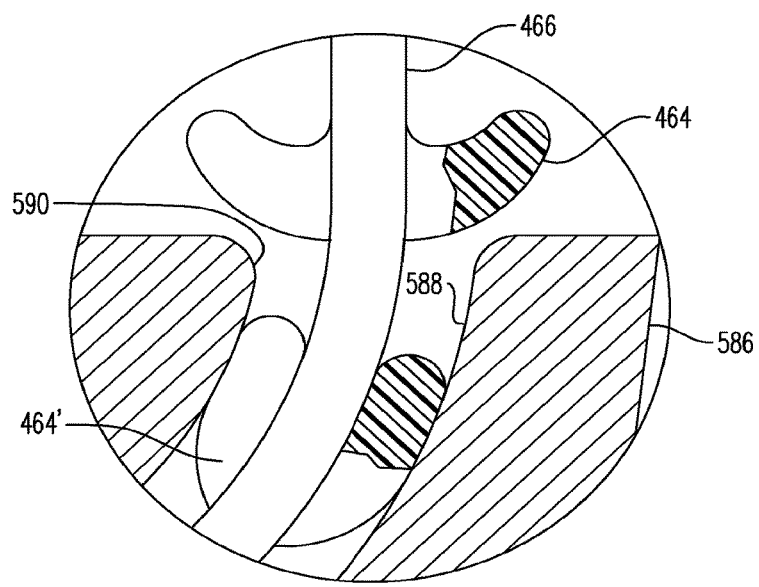
FIG. 84 is an enlargement of area FIG. 84 in FIG. 83.
Figure 88:
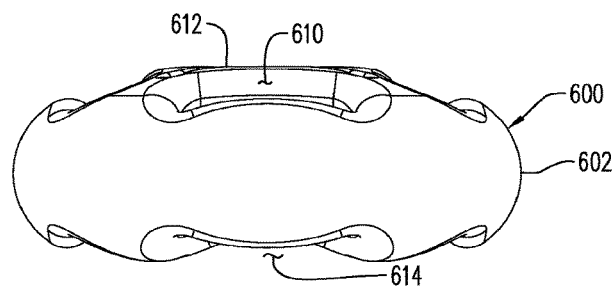
FIG. 88 is an elevation view of FIG. 85.
Figure 89:
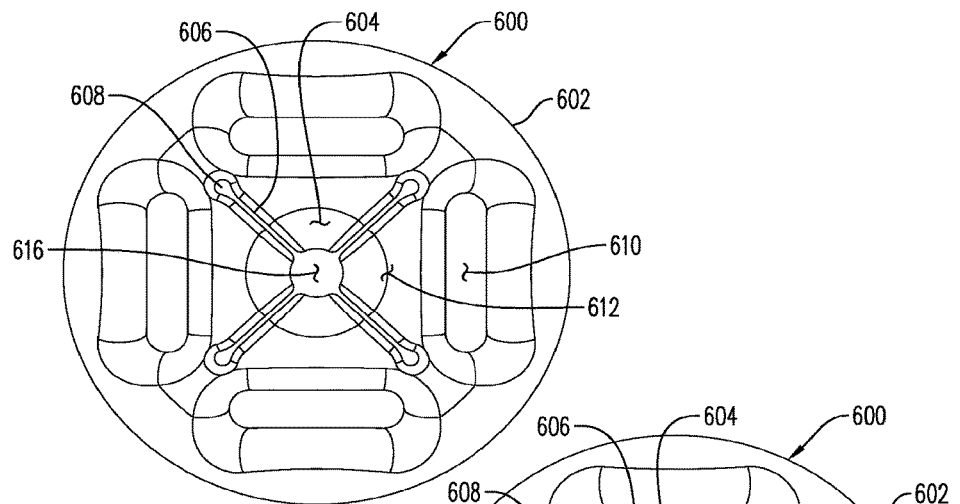
FIG. 89 is a top plan view of FIG. 85.
Figure 90:
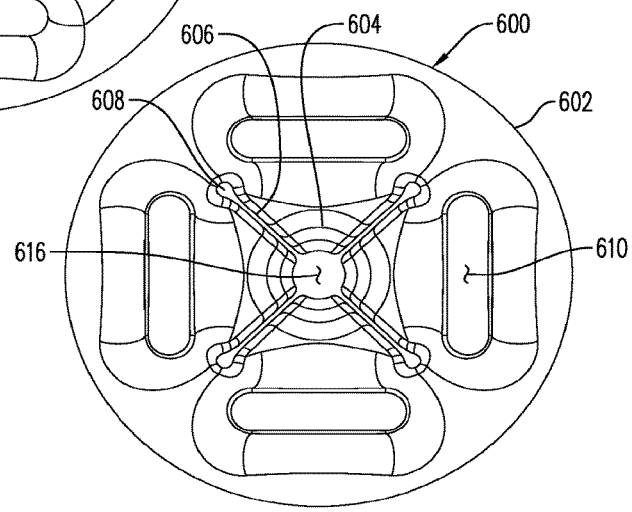
FIG. 90 is a bottom plan view of FIG. 85.

Referring to FIGS. 83 and 84, another embodiment of the tissue anchor is there shown at numeral 580. This exemplary embodiment 580 includes a solid tapered spiral thread 582 having a distal tissue penetrating tip 584 and a tapered head 586 formed having an axially aligned driving socket 594 formed into the proximal end of the tissue anchor 580. This embodiment 580 utilizes the resilient protuberance concept previously described in FIGS. 77 to 82, wherein the suture passage 588 is arcuately configured for smooth passage of the resiliently collapsed protuberances 464' as they are forced against the head deforming inlet surface 590 as the suture is pulled in the direction of the arrow. Reverse movement of the suture is prohibited by the interaction of surface 470 of the backside of each protuberance 464 against the head locking surface 492.

Referring now to the drawings, and firstly to FIGS. 85 to 90, the preferred embodiment of a tissue restraint/suture capture is there shown generally at numeral 600. This tissue restraint/suture capture 600, sometimes referred to herein as a "restraint/capture", is preferably formed of flexible or semi-flexible medically implantable material, such as high density polyethylene, although other suitable material may be utilized. This tissue restraint/suture capture 10 has been shown through computer mathematical analysis to provide for up to preferably a 5:1 ratio of force to move a beaded suture 40 (the suture 40 having spherical or bead-shaped protuberances 44 longitudinally spaced apart along a slender strand 42 and being formed of a flexible, or semi-flexible medically implantable material) through the suture locking aperture 634 of the body 602 in the direction of the arrow shown in FIG. 87 to approximately four times more force to move the suture backward through the locking aperture 604 in the opposite direction. This provides the surgeon performing reattachment surgery the confidence that this tissue restraint/suture capture 600 will maintain the applied force to reconnect adjacent or mating tissues as applied by the surgeon.

Details of this tissue restraint/suture capture 600 were developed initially using Finite Element Analysis (FEA) and its proof-of-concept was bench tested with an Instron, supporting the preliminary FEA findings. The engineering was performed and perfected so failure of the suture/capture system was the suture itself and not the tissue restraint/suture capture. This design 600 also minimizes "GO" three, and maximize "NO-GO" force, the locking aperture 604 specifically engineered to maximize this effect and approaches suture ultimate tensile strength, while the 'GO' forces approximate a simple hand pull. This "NO-GO"/"GO" differential, by minimizing "GO" and maximizing "NO-GO", allows the surgeon to work with confidence with the knowledge that there is no need to pull too hard to get the suture to advance, which could tear the tissue or pull-out the repair, while knowing that the tissue restraint/suture capture 600 can hold the tissue in place with forces approaching the failure strength of the suture.

This tissue restraint/suture capture 600 includes the central suture locking aperture 604 which extends axially and orthogonally to an imaginary plane of the flattened oval shape body 602 and having a locking aperture inlet 614 substantially larger than the diameter of the suture beads 634 for ease of insertion of the tissue restraint/suture capture 600 thereinto. The depth of the inlet side of this suture locking aperture 604 is such that, as best seen in FIG. 87, a portion of the suture strand 632 may be easily grasped during a surgical procedure to begin to pull the suture 630 in the direction of the arrow through the suture locking aperture 604. The locking aperture inlet 614 allows the suture 630 with its beads 634 to approach from various angles thereby allowing more degrees of freedom for the suture 630 to enter the locking aperture 604 without binding, crimping, or bending the suture strand 632.

As each of the suture beads 634 is guided by slot approach 622 and bears against the suture head seat 620, applying further pressure axially to the suture 630 in the direction of the arrow causes the mating inner contour of each of the flex arms 612 (as described more fully herebelow) to flex outwardly (upwardly as viewed in FIG. 3) to expand the locking aperture restriction 616 until the desired number of suture bead 634 are pulled therethrough, after which the flex arms 612 automatically and resiliently return to the at rest position, collapsing the locking aperture restriction 616. Importantly the outlet end of the suture locking aperture 604 includes a reverse restriction 618 which serves to insure that the suture 630 may not be moved in the opposite ("NO-GO") direction from the arrow without applying a pulling force typically necessary to fracture the suture strand 632, the flex arms 612 resiliently flexing inwardly in the reverse suture pulling direction to narrow the locking restriction aperture 616.

Each of the flex arms 612 is defined by adjacent radially extending radial slots 606 each of which terminate at the outer end thereof in an enlarged slot relief hole 608. Each of the flex arms 612 has a greater radial thickness at the exit side 618 of the body 602 relative to the radial thickness at the inlet side 614 of the body 602 for defining the central locking aperture 604 with the inlet side 614 being substantially larger than the exit side 618 of the central locking aperture 604. Preferably, the flex arms 612 curve radially inwardly from the inlet side 614 to the exit side 618 of the body 602. Each of the flex arms 612 is further defined by an elongated oval or racetrack-shaped elongated flex arm slot 610. Each of the plurality of flex arms 612 decreasing in thickness from an outer end 610 to an inner end 618 of the flex arm 612. Each inner corner of each of the flex arm slots 610 is formed in proximity to one of the slot relief holes 608, the spacing therebetween having a substantial influence on the overall flexibility of each of the flex arms 612 as the suture 630 and each of its suture beads 634 is pulled through the suture locking aperture 604 as previously described.

Figure 91:
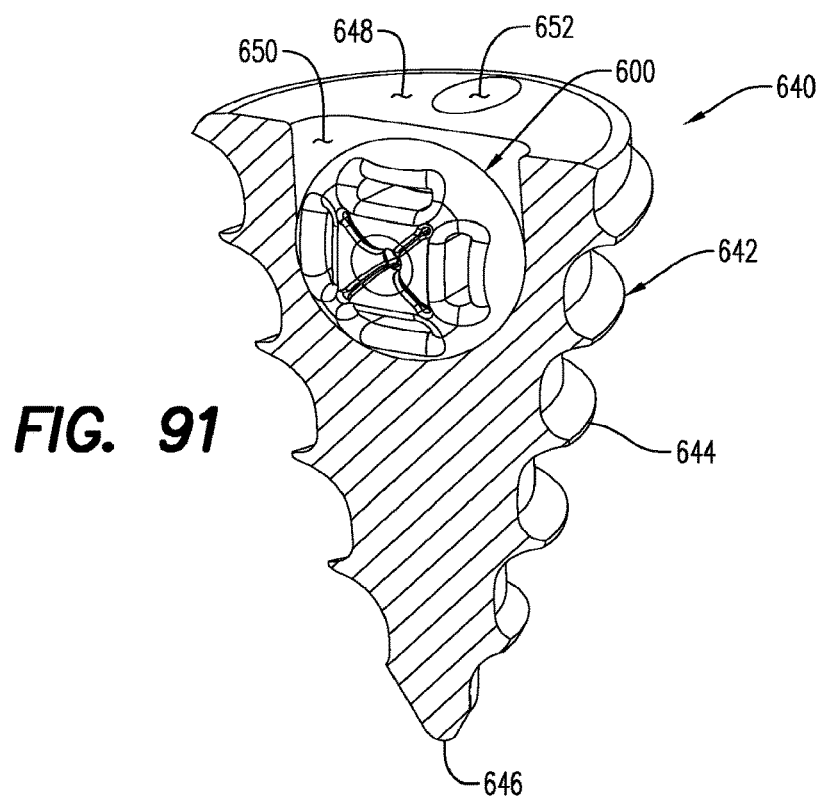
FIG. 91 is a perspective section view of a suture anchor configured to receive the tissue restraint/suture capture 600 of FIG. 85.
Figure 92:
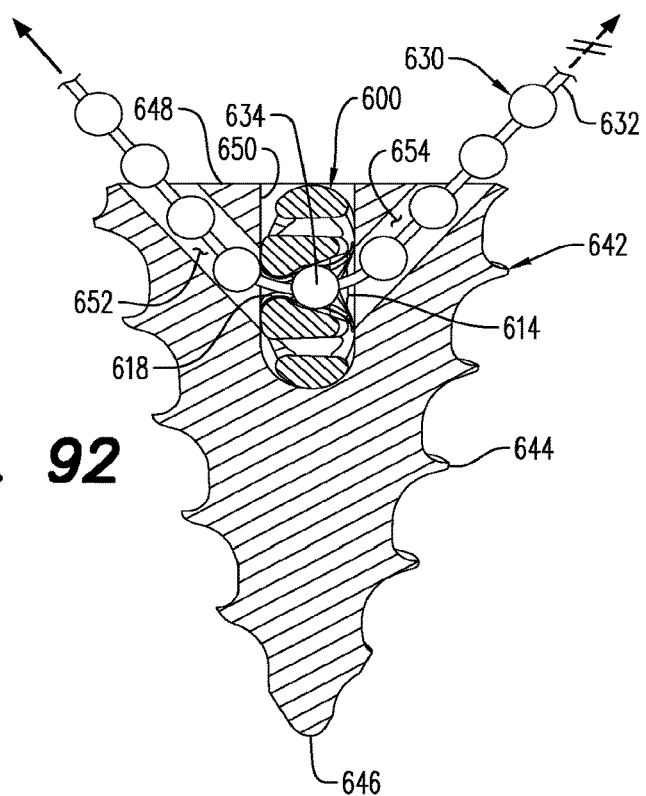
FIGS. 92 to 94 are side elevation section views of other embodiments of the suture anchor showing the tissue restraint 600 of FIG. 85 lockingly engaged with the beaded suture 630.

Referring now to FIGS. 91 and 92, a first embodiment of the combination of the previously described tissue restraint/suture capture 600 and a tissue anchor 642 is there shown generally at numeral 640. The tissue anchor 642, preferably formed of surgically implantable material suitably formed to be rotatably driven into cartilage or bone, includes a tapered spiral thread 644 and a tissue penetrating tip 646 for ease of piercing through the tissue material as the tissue anchor 642 is rotatably driven into and secured within the cartilage or bone material.

The head 648 of the tissue anchor 642 includes a longitudinally extending restraint receiving cavity 650 formed to tightly and wedgingly receive the tissue restraint/suture capture 600 into the position best seen in FIG. 92. Diagonally extending suture entrance and exit passages 654 and 652 are provided so that the suture 630 may be easily inserted through the suture locking aperture 604 of the tissue restraint/suture capture 600 through the suture entrance passage 654, exiting from the suture exit passage 652. After the tissue anchor 642 has been secured within the tissue by being rotationally driven as facilitated by the openings of each of the passages 652 and 654, the suture 630 may be inserted into the position shown in FIG. 92 and then tensioned as desired. Again, by the structural benefits of the tissue restraint/suture capture 600 as previously described, movement of the suture 630 is only possible, preferably without suture fracture, in the direction of the arrow from the suture exit passage 652.

Figure 93:
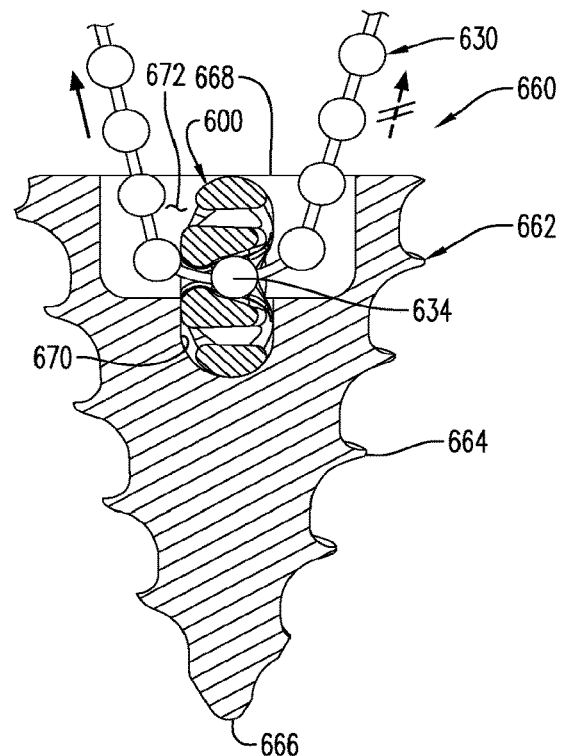

Referring now to FIG. 93, another embodiment of the combination of the suture tissue restraint/suture capture 600 and a tissue anchor 662 is there shown at generally at numeral 660. In this embodiment 660, the tissue anchor 662, having tapering spiral threads 664 and a tissue penetrating tip 666 as previously described, includes a restraint receiving cavity 670 which tightly and wedgingly receives a portion of the tissue restraint/suture capture 600 in an upright orientation. However, an enlarged suture clearance cavity 672 formed axially downwardly into the head 668 is provided for free access of the suture 630 into and from the suture locking aperture 604.

Figure 94:
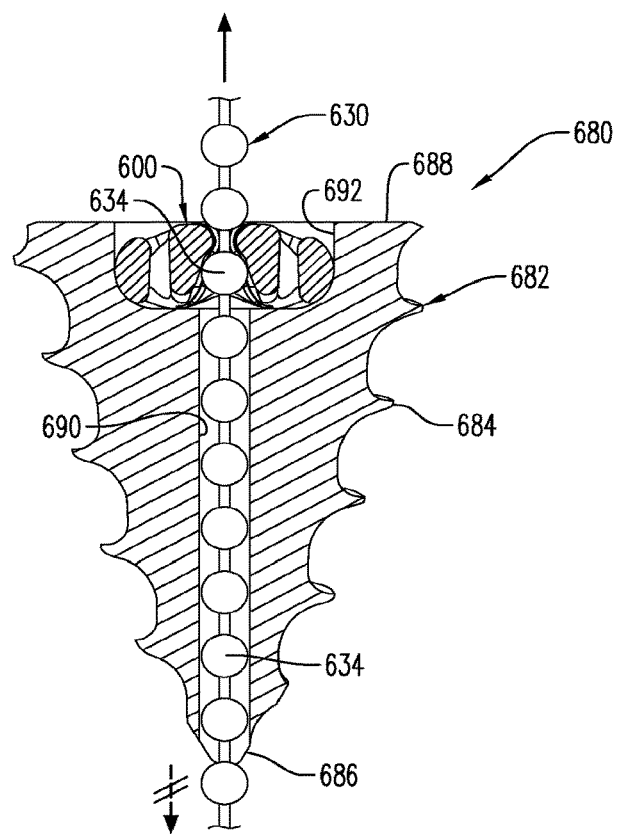

In FIG. 94, yet another embodiment of the combination of a tissue anchor 682 and the tissue restraint/suture capture 600 is there shown generally at numeral 680. In this embodiment 680, the tissue restraint/suture capture 600 is oriented transversely to the longitudinal axis of the tissue anchor 682, the tissue restraint/suture capture 600 being tightly and wedgingly secured into a generally circular restraint receiving cavity 692 formed into the head 688 of the tissue anchor 682. To facilitate smooth and easy access of the suture 630 through the suture locking aperture 604, an elongated longitudinally extending suture passage 690 is provided. In this embodiment 680, the tissue anchor 682 may be secured into the tissue after the suture 630 has been fed from the opposite side of the anchoring tissue and then fed through the suture passage 690 and the suture locking aperture 604 of the tissue anchor 682 for tensioning in the direction of the arrow. Note that the force applied downwardly on the tissue restraint/suture capture 600 after proper tensioning of the suture 630 will enhance maintaining the tissue restraint/suture capture 600 within the suture receiving cavity 692.

Figure 95:
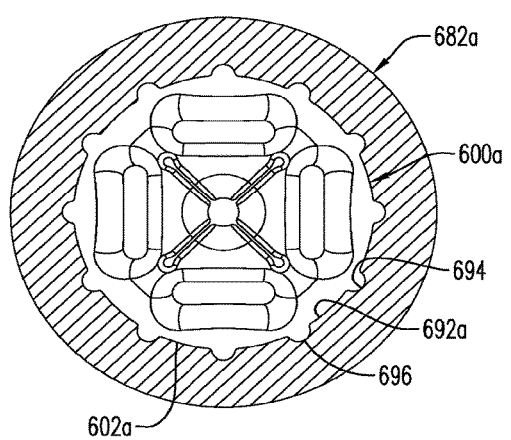
FIGS. 95 and 96 are top plan section views of other embodiments of the suture anchor showing alternate embodiments of the tissue restraint of FIG. 85 lockingly engaged therein.
Figure 96:
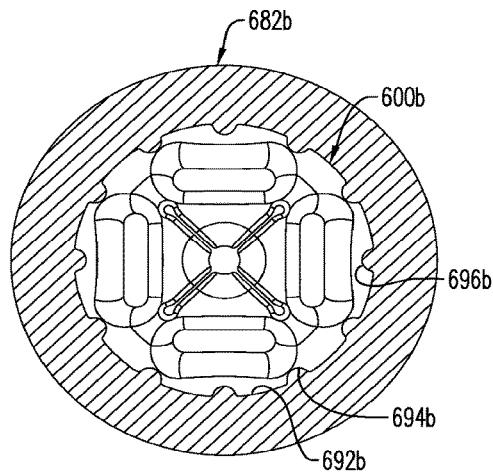
Figure 97:
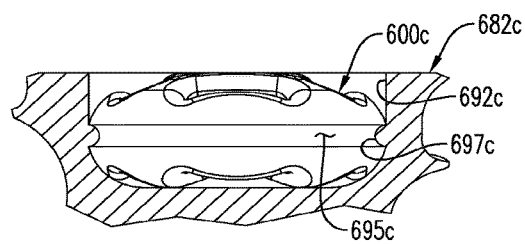
FIGS. 97 and 98 are broken elevation section views of the enlarged ends of other embodiments of the suture member showing alternate embodiments of the tissue restrain/suture capture of FIG. 85 lockingly engaged therein.
Figure 98:
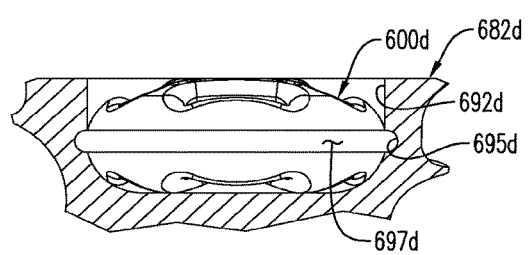

Referring now to FIGS. 95 to 98, rather than relying only upon the tight, frictional wedging retention of the tissue restraint/suture capture 600a, b, c, d within the cavity formed into the head of a tissue anchor, four separate additional structural features are thereshown. In FIG. 95, the head of the tissue anchor 682a includes indents 694 which securely engage with spaced dimples 696 which outwardly extend from the perimeter of the body 602a of the tissue restraint/suture capture 600a. In FIG. 96, the reverse structural feature is provided wherein dimples 696b extend inwardly from the restraint receiving cavity 692b to engage into indents 694b formed into the body of the tissue restraint/suture capture 600b. In FIG. 97, an annular groove 695c is formed into the periphery of the body of tissue restraint/suture capture 600c which snappingly engages with an annular bead 697c formed inwardly from the restraint receiving cavity 692c. In FIG. 98, the reverse structure having the annular bead 697d formed outwardly extending from the body of the tissue restraint/suture capture 600d matingly engages into the annular groove 695d formed into the restraint receiving cavity 692d. Other interfering structure to effect this locking engagement is also anticipated within the scope of this disclosure.

Figure 99:
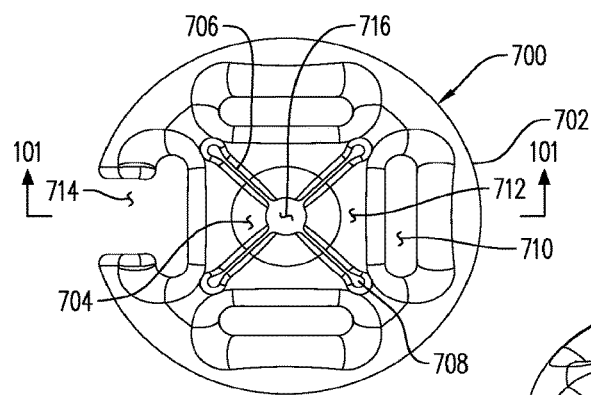
FIG. 99 is a top plan view of another embodiment of the tissue restraint/suture capture of FIG. 85.
Figure 100:
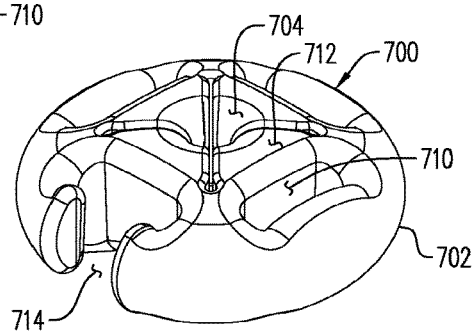
FIG. 100 is a perspective view of FIG. 99.
Figure 101:
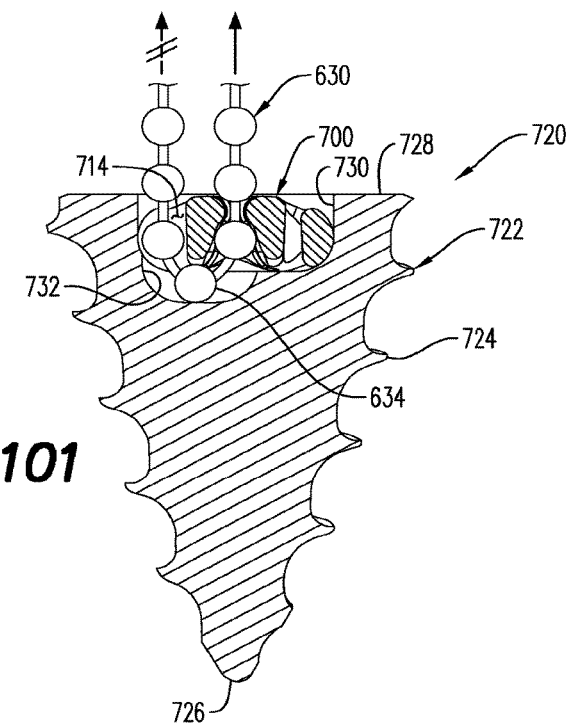
FIG. 101 is a section view in the direction of arrows 101-101 in FIG. 99 showing the beaded suture 630.

Alternate forms of suture clearances are shown in FIGS. 99 to 104 in conjunction with uniquely configured heads 728 and 728' of tissue anchors 722 and 722'. In FIGS. 99 and 100, a suture clearance notch 714 is formed into the periphery of the body 702 directly into one of the flex arm relief holes 710. This clearance notch 714 is sufficiently wide for the suture 630 to pass thereinto when the tissue restraint/suture capture 700 is secured into the restraint receiving cavity 630 formed into the head 728 of the tissue anchor 722. An additional suture clearance cavity 732 is provided so that the suture 630 may be reversed as it is inserted into the locking aperture of the tissue restraint/suture capture 700. This tissue anchor 722 as previously described, also includes the tapered spiral threads 724 and the tissue penetrating tip 726.

Figure 102:
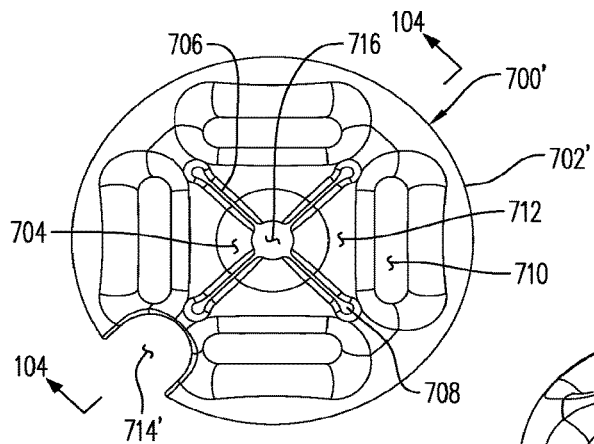
FIG. 102 is a top plan view of another embodiment of the tissue restraint of FIG. 85.
Figure 103:
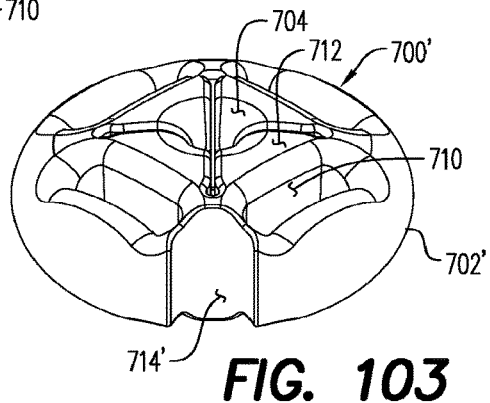
FIG. 103 is a perspective view of FIG. 102.
Figure 104:
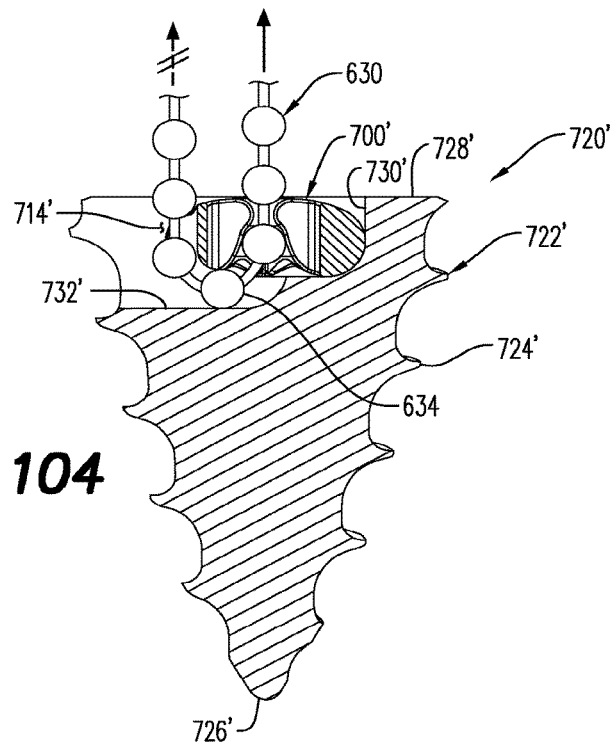
FIG. 104 is a section view in the direction of arrows 104-104 in FIG. 102 showing the beaded suture 630.

In FIGS. 102 to 104, the combination of the tissue restraint/suture capture 700' and the tissue anchor 722' is shown in combination at 720'. The tissue restraint/suture capture 700' is structurally generally as previously described except for having the suture clearance notch 714' formed into the periphery of the body 702' directly radially outwardly from one of the slot relief holes 708 disposed at the radially outward end of the corresponding radial slot 706. Again, the suture clearance notch 714' has sufficient width and depth so that the suture 630 will pass thereinto with additional clearance by suture clearance cavity 732' to reverse the suture direction to pass into the tissue restraint/suture capture 700' which has been secured into the restraint receiving cavity 730' formed into the head 728' of the tissue anchor 722'.

Figure 105:
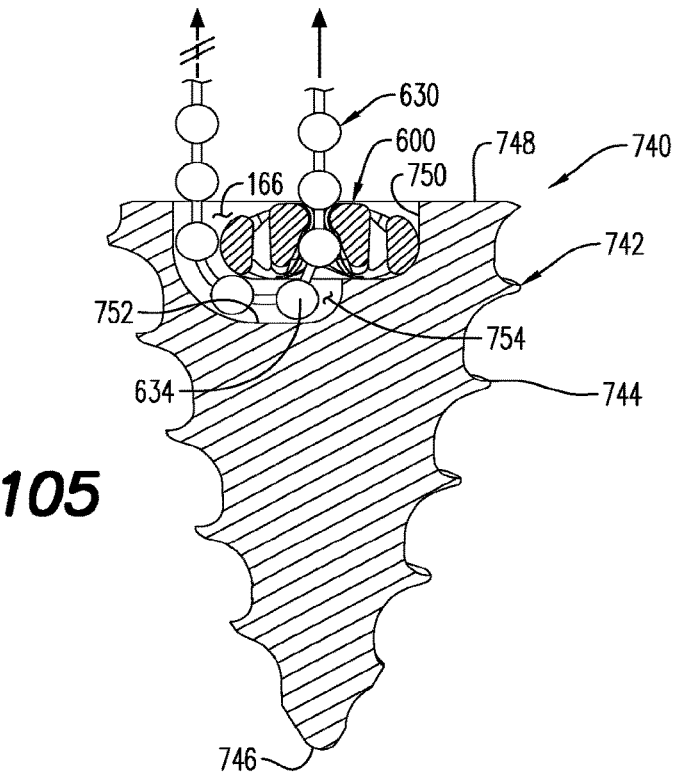
FIGS. 105 and 106 are side elevation section views of other embodiments of suture anchors showing the tissue restrain/suture capture 600 of FIG. 85 lockingly engaged therein showing the beaded suture 630.

Still another arrangement for the locking interengagement between the suture tissue restraint/suture capture 600 and a tissue anchor 742 is there shown generally at numeral 740 in FIG. 105. In this embodiment 740, the tissue restraint/suture capture 600 is lockingly engaged into a mating restraint receiving cavity 750 and a suture clearance cavity 752 having a bead clearance area at 754 and a bead exit area 756 is also provided for the smooth introduction of the suture 630 first downwardly into the bead exit area 756 and then upwardly from the locking aperture of the tissue restraint/suture capture 600. The tissue anchor 742 similarly includes tapered spiral thread 744 and a tissue penetrating tip 746 as previously described.

Figure 106:
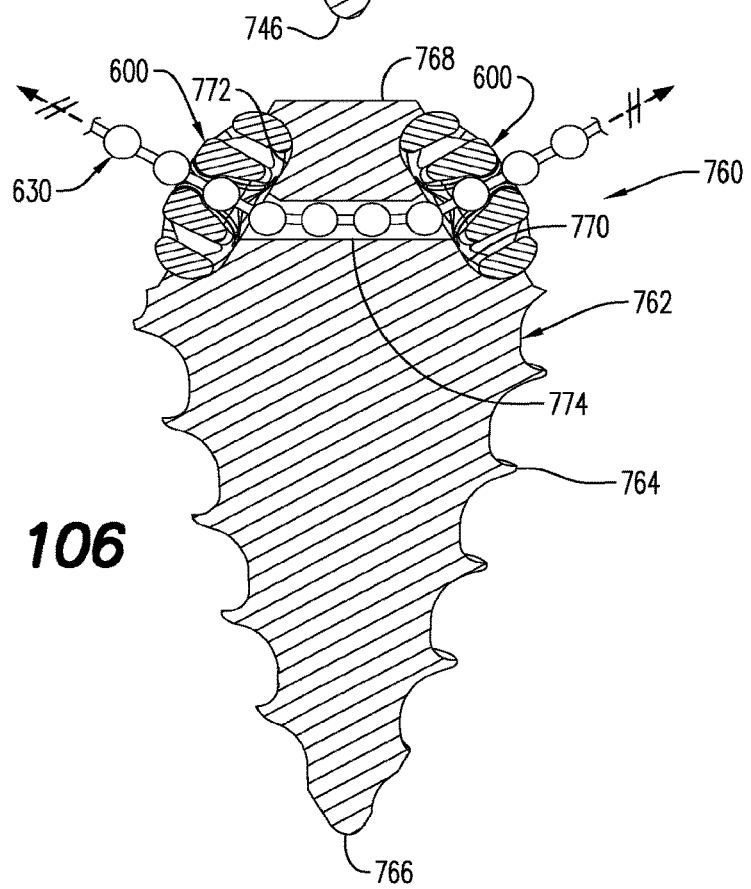
Figure 107:
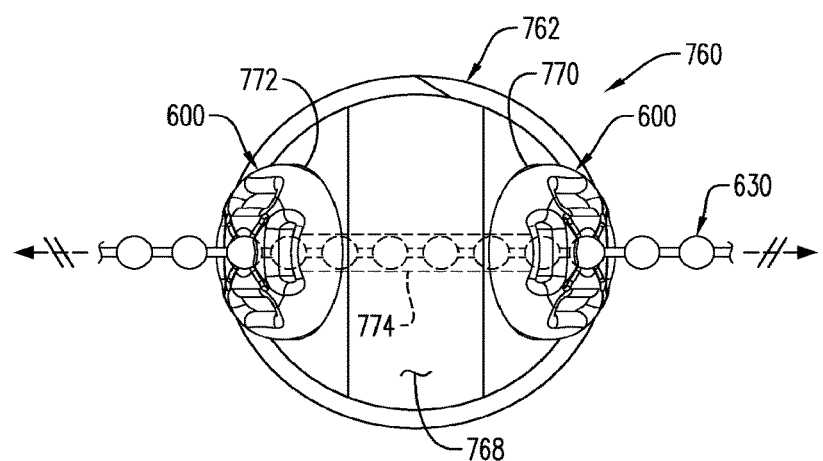
FIG. 107 is a top plan view of FIG. 106.

In FIGS. 106 and 107, a tissue anchor 762 with dual opposing restraints/captures 600 is shown generally at numeral 760. In this embodiment 760, opposing tissue restraints/suture captures 600 are secured within diagonally oriented opposing restraint receiving cavities 770 and 772 such that the suture 630 may be lockingly passed through one of the tissue restraints/suture captures 600, then through a connecting suture passage 774 and then into an through the opposing tissue restraint/suture capture 600. Note that, in this embodiment 760, the suture 630 is restrained from any movement whatsoever with respect to the head 768 of the tissue anchor 762, requiring that the suture 630 be first passed through one of the tissue restraints/suture captures 600 then through suture passage 774 and then tensioned through the second tissue restraint/suture capture 600 after it has been positioned in its restraint receiving cavity 772. Alternately, each tissue restraint/suture capture 600 (in this embodiment 760, a suture capture) may be slid down the suture 630 on each side of the tissue anchor 762 and locked in place as shown rather than having the suture 630 pass through the suture 630 pass through the suture passage 608 with the tissue restraint/suture captures 600 already in place. Another arrangement envisions reversing one of restraint/suture captures 600, allowing the suture 630 to travel in only one direction through one tissue restraint/suture capture 600, then through the suture passage 774 and out through the second tissue restraint/suture capture 600 for enhanced "NO-GO" strength.

Figure 108:
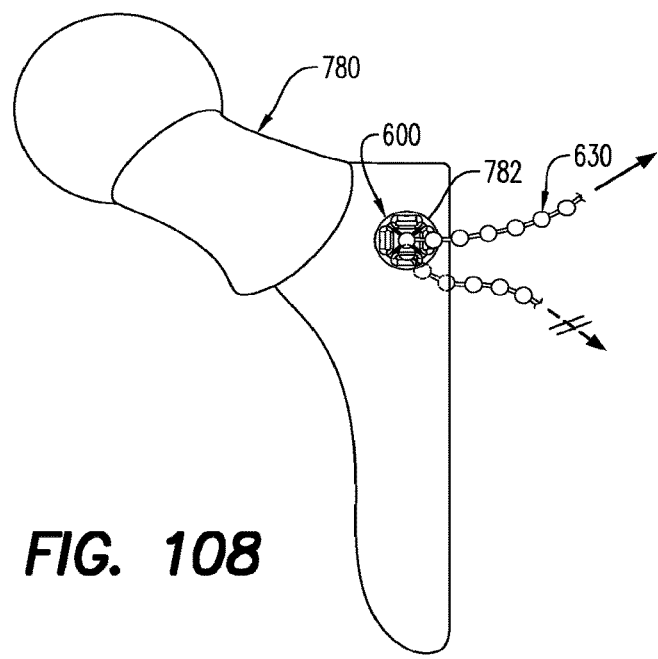
FIG. 108 is a pictorial view of the tissue restraint of FIG. 85 lockingly engaged with a typical surgically implanted device showing the beaded suture 630.

Lastly, in FIG. 108, the tissue restraint/suture capture 600 is shown secured into a mating restraint receiving cavity 782 formed into a prosthetic implant 780. This concept is intended to shown that the tissue restraint/suture capture 10 or any suitable variation thereof within the scope of this invention may be secured into any medically, veterinary, dental implantable prosthesis implant such as a pacemaker, heart valve, or stent, veterinary or medical dental bone plate, breast implant, gastrointestinal ligature or ligature type device or any other medically, veterinary, dental implantable device which either requires suture restraint or will provide a suture restraint for a suture to pass therethrough. Thus, the tissue restraint/suture capture 600, as opposed to being utilized as a tissue restraint alone or with an anchor, may be used as a suture capture incorporated into other medical, veterinary or dental implants.

While a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

The invention claimed is:

1. In a surgical suture system for tissue repair and reattachment of torn tissue to a tissue substrate or medical, veterinary or dental implant including an elongated flexible suture having a plurality of longitudinally spaced protuberances along a length thereof, the improvement comprising:
a tissue restraint/suture capture comprising a body defining an inlet side and an exit side;
a central locking aperture disposed in a central region of said body;
a plurality of spaced apart radial slots extending outwardly from said central locking aperture for defining a plurality of flex arms with an inner end of each of said flex arms defining said central locking aperture;
each of said inner ends of said plurality of flex arms curving radially inwardly from said inlet side to said exit side of said body for defining said inlet side of said central locking aperture to be substantially larger than said exit side of said central locking aperture;
said plurality of flex arms cooperating with said inlet side of said central locking aperture enabling said plurality of flex arms to flex outwardly to permit entrance and longitudinal movement of the plurality of longitudinally spaced protuberances of the suture in a forward direction into said inlet side of said central locking aperture with minimal force; and
said plurality of flex arms cooperating with said exit side of said central locking aperture enabling said plurality of flex arms to flex inwardly to inhibit the movement of the plurality of longitudinally spaced protuberances of the suture in a reverse direction.

2. In a surgical suture system for tissue repair and reattachment as set forth in claim 1, wherein said body has a generally oval cross-section with a central region of said body being thicker than a peripheral region of said body.

3. In a surgical suture system for tissue repair and reattachment as set forth in claim 1, wherein each of said plurality of spaced apart radial slots extends radially outwardly from said central locking aperture and terminates at an outer end; and
a slot relief hole located at each of said outer ends of said plurality of spaced apart radial slots.

4. In a surgical suture system for tissue repair and reattachment as set forth in claim 1, wherein each of said plurality of spaced apart radial slots extends radially outwardly from said central locking aperture and terminates at an outer end; and
an elongated flex arm slot located between adjacent outer ends of said plurality of spaced apart radial slots for defining outer ends of said plurality of flex arms.

5. In a surgical suture system for tissue repair and reattachment as set forth in claim 1, wherein each of said plurality of spaced apart radial slots extends radially outwardly from said central locking aperture and terminates at an outer end;
an elongated flex arm slot located between adjacent outer ends of said plurality of spaced apart radial slots, and said each of said flex arm being bounded by adjacent radial slots and adjacent elongated flex arm slot and said central locking aperture.

6. In a surgical suture system for tissue repair and reattachment as set forth in claim 1, wherein said central locking aperture provides a differential force ratio between the force required to move the suture in the reverse direction, a "NO-GO" force, and the force required to move the suture in the forward direction, a "GO" force exceeding a 1.5:1 ratio.

7. In a surgical suture system for tissue repair and reattachment of torn tissue to a tissue substrate or medical, veterinary or dental implant including an elongated flexible suture having a plurality of longitudinally spaced protuberances along a length thereof, the improvement comprising:
a tissue restraint/suture capture comprising a body defining an inlet side and an exit side;
a central locking aperture disposed in a central region of said body;
a plurality of spaced apart radial slots extending outwardly from said central locking aperture for defining a plurality of flex arms;
an inner end of each of said plurality of flex arms defining said central locking aperture;
a plurality of elongated flex arm slots defining outer ends of said plurality of flex arms;
each of said plurality of flex arms curving radially inwardly from said inlet side to said exit side of said body for defining said central locking aperture with said inlet side being substantially larger than the longitudinally spaced protuberances and with said exit side being substantially smaller than the longitudinally spaced protuberances;
said plurality of flex arms cooperating with said inlet side of said central locking aperture enabling said plurality of flex arms to flex outwardly to permit entrance and longitudinal movement of the plurality of longitudinally spaced protuberances of the suture in a forward direction into said inlet side of said central locking aperture with minimal force; and
said plurality of flex arms cooperating with said exit side of said central locking aperture enabling said plurality of flex arms to flex inwardly to inhibit the movement of the plurality of longitudinally spaced protuberances of the suture in a reverse direction.

8. In a surgical suture system for tissue repair and reattachment as set forth in claim 7, wherein said body has a generally oval cross-section with said central region of said body being thicker than a peripheral region of said body.

9. In a surgical suture system for tissue repair and reattachment as set forth in claim 7, wherein each of said plurality of spaced apart radial slots extends radially outwardly from said central locking aperture and terminates at an outer end; and
a slot relief hole located at each of said outer ends of said plurality of spaced apart radial slots.

10. In a surgical suture system for tissue repair and reattachment of torn tissue to a tissue substrate or medical, veterinary or dental implant including an elongated flexible suture having a plurality of longitudinally spaced protuberances along a length thereof, the improvement comprising:
a tissue restraint suture capture comprising a body defining an inlet side and an exit side;
a central locking aperture disposed in a central region of said body;

a plurality of spaced apart radial slots extending outwardly from said central locking aperture for defining a plurality of flex arms;

each of said flex arms extending from an inner end of said flex arm defining said central locking aperture to an outer end;

each of said inner ends of said flex arms curving radially inwardly along an axial distance from said inlet side to said exit side of said body for defining said central locking aperture with said inlet side being substantially larger than said exit side of said central locking aperture;

said flex arms cooperating with said inlet side of said central locking aperture enabling said flex arms to flex outwardly to permit entrance and longitudinal movement of the plurality of longitudinally spaced protuberances of the suture in a forward direction into said inlet side of said central locking aperture with minimal force; and said flex arms cooperating with said exit side of said central locking aperture enabling said flex arms to flex inwardly to inhibit the movement of the plurality of longitudinally spaced protuberances of the suture in a reverse direction.

\* \* \* \* \*